United States Patent
Muchero et al.

(10) Patent No.: US 11,028,404 B2
(45) Date of Patent: Jun. 8, 2021

(54) METHODS OF IMPROVING MYCORRHIZATION IN PLANTS AND GENETICALLY MODIFED PLANTS WITH IMPROVED MYCORRHIZATION

(71) Applicants: UT-Battelle, LLC, Oak Ridge, TN (US); University of Tennessee Research Foundation, Memphis, TN (US)

(72) Inventors: Wellington Muchero, Oak Ridge, TN (US); Jessy L. Labbe, Oak Ridge, TN (US); Lee E. Gunter, Oak Ridge, TN (US); Jin-Gui Chen, Oak Ridge, TN (US); Sara S. Jawdy, Oak Ridge, TN (US); Xiaohan Yang, Knoxville, TN (US); Gerald A. Tuskan, Oak Ridge, TN (US); Juan Wang, Oak Ridge, TN (US); Olaf Czarnecki, Oak Ridge, TN (US); Priya Ranjan, Knoxville, TN (US)

(73) Assignees: UT-Battelle, LLC, Oak Ridge, TN (US); University of Tennessee Research Foundation, Memphis, TN (US)

(*) Notice: Subject to any disclaimer, the term of this patent is extended or adjusted under 35 U.S.C. 154(b) by 0 days.

(21) Appl. No.: 16/520,967

(22) Filed: Jul. 24, 2019

(65) Prior Publication Data
US 2020/0032285 A1    Jan. 30, 2020

Related U.S. Application Data

(60) Provisional application No. 62/703,934, filed on Jul. 27, 2018.

(51) Int. Cl.
*C12N 15/82* (2006.01)
*C12N 9/12* (2006.01)

(52) U.S. Cl.
CPC .......... *C12N 15/8261* (2013.01); *C12N 9/12* (2013.01); *C12Y 207/11001* (2013.01)

(58) Field of Classification Search
None
See application file for complete search history.

(56) References Cited

U.S. PATENT DOCUMENTS

2016/0017345 A1    1/2016   Herrera-Estrella et al.
2017/0121722 A1    5/2017   Anand et al.

FOREIGN PATENT DOCUMENTS

WO    2015/095186 A2    6/2015

OTHER PUBLICATIONS

Wang et al. Plant Cell Rep(2016)35:845-855.*
Wu, Y. et al., "Receptor-Like Kinases in Plant Innate Immunity", Journal of Integrative Plant Biology, Oct. 29, 2013, vol. 55, No. 12, pp. 1271-1286.
Antolin-Llovera, M. et al., "Knowing your Friends and Foes—Plant Receptor-Like Kinases as Initiators of Symbiosis or Defence", New Phytologist, 2014, vol. 204, pp. 791-802.
Labbe, J. et al., "Identification of Quantitative Trait Loci Affecting Ectomycorrhizal Symbiosis in an Interspecific $F_1$ Poplar Cross and Differential Expression of Genes in Ectomycorrhizas of the Two Parents: Populus deltoides and Populus trichocarpa", Tree Genetics & Genomes 2011, vol. 7, pp. 617-627.
Courty, P. E. et al., "Effect of Poplar Genotypes on Mycorrhizal Infection and Secreted Enzyme Activities in Mycorrhizal Andnon-Mycorrhizal Roots", Journal of Experimental Botany, Sep. 29, 2011, vol. 62, No. 1, pp. 249-260.
Gottel, N. R. et al., "Distinct Microbial Communities within the Endosphere and Rhizosphere of Populus deltoides Roots across Contrasting Soil Types", Applied and Environmental Microbiology, Jul. 2, 2011, vol. 77 No. 17, pp. 5934-5944.
Martin, F. et al., "Unearthing the Roots of Ectomycorrhizal Symbioses", Nature Reviews, Microbiology, 2016, vol. 14, pp. 760-773.
Kohler, A. et al., "Convergent losses of decay mechanisms and rapid Turnover of Symbiosis Genes in Mycorrhizal Mutualists", Nature Genetics, 2015, vol. 47, pp. 410-415.
Tagu, D. et al., "Variation in the Ability to Form Ectomycorrhizas in the F1 Progeny of an Interspecific Poplar (*Populus* spp.) Cross," Mycorrhiza, 2001, vol. 10, pp. 237-240.
Chen X.Y, et al., "Callose synthesis in higher plants", Plant Signaling & Behavior, 4:6, pp. 489-492 (Jun. 2009).
Liu P.L., et al., "Duplication and diversification of lectin receptor-like kinases (LecRLK) genes in soybean", Scientific Reports, 8:5861, 14 pages (2018).
International Search Report dated Nov. 5, 2019 issued in PCT/US2019/043223.
Nguyen, V. P., et al, "Identification and Functional Analysis of a Promoter Sequence for Phloem Tissue Specific Gene Expression from Populus trichocarpa", J. Plant Biol., 2017, pp. 129-136, 60.
Nguyen, V. P., et al, "Evaluation of a novel promoter from Populus trichocarpa for mature xylem tissue specific gene delivery", Plant Physiology and Biochemistry, Mar. 2016, pp. 226-233, 104.
Vaid, N., et al., "Knights in Action: Lectin Receptor-Like Kinases in Plant Development and Stress Responses", Molecular Plant, Sep. 2013, pp. 1405-1418, vol. 6, No. 5.
Zhou, J., et al., "Specific Expression of DR5 Promoter in Rice Roots Using a tCUP Derived Promoter-Reporter System", PLOS One, Jan. 22, 2014, 12 pages, vol. 9, Issue 1.

* cited by examiner

*Primary Examiner* — Medina A Ibrahim
(74) *Attorney, Agent, or Firm* — Scully, Scott, Murphy & Presser, P.C.

(57) ABSTRACT

The present disclosure is directed to methods of improving mycorrhization in a plant or plant cell. Another aspect of this disclosure is directed to a genetically modified plant or plant cell with improved mycorrhization.

19 Claims, 8 Drawing Sheets
(8 of 8 Drawing Sheet(s) Filed in Color)
Specification includes a Sequence Listing.

A

| GeneID | Col_1 | Col_2 | Col_3 | Col_lactate_1 | Col_lactate_2 | Col_lactate_3 | 1 | 2 | 3 |
|---|---|---|---|---|---|---|---|---|---|
| AT1G02930 | 89 | 112 | 97.9 | 152.74 | 115.7 | 108.43 | 225 | 200 | 118 | 105.92 | 82.95 | 83.47 |
| AT1G18590 | 23 | 21.7 | 15.8 | 33.71 | 32.03 | 35.71 | 34.3 | 25.8 | 23.8 | 32.54 | 27.03 | 28.28 |
| AT1G21250 | 6.97 | 9.01 | 5.88 | 7.11 | 7.16 | 10.56 | 26.1 | 23.2 | 12.5 | 5.91 | 9.43 | 9.82 |
| AT1G23740 | 10.7 | 13.7 | 15.9 | 10.91 | 10.54 | 10.74 | 18.2 | 17.7 | 19.7 | 9.67 | 10.57 | 11.69 |
| AT1G24100 | 59.3 | 63.5 | 49.9 | 88.21 | 82.34 | 86.47 | 78.3 | 61.7 | 55 | 74.69 | 70.11 | 62.71 |
| AT1G52030 | 0.65 | 0.46 | 0.21 | 0.6 | 0.59 | 0.38 | 0.94 | 2.65 | 0.63 | 0.35 | 0.07 | 0.28 |
| AT1G52040 | 0.91 | 0.4 | 0.21 | 0.87 | 0.67 | 0.56 | 1.25 | 4.18 | 1.1 | 0.59 | 0.09 | 0.34 |
| AT1G72930 | 18.5 | 21.4 | 20.4 | 17.76 | 15.3 | 26.11 | 39.5 | 42.9 | 32 | 16.92 | 23.99 | 25.68 |
| AT1G75040 | 9.14 | 7.75 | 6.36 | 7.45 | 8.58 | 5.23 | 8.39 | 9.03 | 7.79 | 4.32 | 3.84 | 5.47 |
| AT2G02130 | 236 | 216 | 180 | 125.29 | 152.45 | 151.88 | 141 | 153 | 176 | 150.85 | 124.83 | 126.34 |
| AT2G14560 | 17 | 17 | 5.38 | 18.49 | 26.59 | 24.67 | 52.4 | 33.7 | 21.6 | 8.35 | 12.59 | 13.27 |
| AT2G14610 | 9.03 | 1.82 | 0.55 | 5.03 | 26.9 | 14.57 | 44.6 | 15.5 | 38.4 | 1.66 | 1.09 | 1.87 |
| AT2G20610 | 36.3 | 37.9 | 32.9 | 52.68 | 48.84 | 52.98 | 49 | 36.2 | 34.9 | 45.26 | 44.76 | 39.91 |
| AT2G25110 | 44.6 | 45.2 | 44.3 | 45.42 | 47.32 | 47.35 | 49.1 | 42.9 | 35.1 | 37.73 | 30.53 | 28.65 |
| AT2G29350 | 2.13 | 1.43 | 0.76 | 1.55 | 1.39 | 1.83 | 5.36 | 7.45 | 3.48 | 1.34 | 0.84 | 1.36 |
| AT2G38860 | 62.8 | 59 | 45.1 | 95.76 | 89.11 | 88.45 | 84.5 | 64.5 | 50 | 78.84 | 67.92 | 61.44 |
| AT2G38870 | 30.3 | 34.7 | 29.3 | 35.4 | 30.53 | 38.76 | 34 | 36.7 | 32.3 | 20.45 | 23.41 | 27.18 |

| GeneID | Col 1 | Col 2 | Col 3 | Col_laccase-1 | Col_laccase-2 | Col_laccase-3 | | | | | | |
|---|---|---|---|---|---|---|---|---|---|---|---|---|
| AT2G42530 | 4.4 | 34.6 | 12.1 | 11.04 | 27.82 | 13.83 | 64.2 | 76.4 | 81.7 | 7.69 | 5.6 | 16.53 |
| AT2G42540 | 18.9 | 15.1 | 1.48 | 5.71 | 20.82 | 4.18 | 48.8 | 72.5 | 38.8 | 5.21 | 1.33 | 7.88 |
| AT2G46650 | 27.5 | 28.2 | 22.1 | 39.64 | 35.63 | 42.13 | 35.2 | 22.1 | 31 | 44.8 | 38.43 | 35.47 |
| AT3G04210 | 8.59 | 7.27 | 7.27 | 8.82 | 8.47 | 8.8 | 14.1 | 14.2 | 13.5 | 8.47 | 9.41 | 10.9 |
| AT3G09840 | 174 | 163 | 146 | 150.07 | 162.53 | 151.23 | 161 | 153 | 140 | 138.79 | 123.75 | 122.99 |
| AT3G28740 | 63.8 | 61.4 | 73.9 | 68.95 | 75.33 | 72.06 | 53.2 | 50.9 | 56.9 | 77.79 | 76.24 | 73.77 |
| AT3G28940 | 281 | 273 | 226 | 371.5 | 351.74 | 351.42 | 353 | 328 | 255 | 313.22 | 306.7 | 290.05 |
| AT3G52960 | 153 | 163 | 181 | 150.64 | 144.53 | 161.23 | 171 | 166 | 176 | 138.12 | 136.05 | 140.27 |
| AT3G60420 | 1.28 | 1.06 | 1.31 | 1.36 | 0.99 | 1.77 | 3.09 | 2.61 | 2.35 | 0.91 | 0.93 | 1.27 |
| AT3G63380 | 6.02 | 3.94 | 4.15 | 3.72 | 4.5 | 4.98 | 9.05 | 8.6 | 6.42 | 3.23 | 3.49 | 5.82 |
| AT4G08870 | 3.06 | 3.1 | 3.11 | 3.67 | 2.51 | 3.49 | 5.47 | 7.62 | 4.35 | 2.37 | 2.35 | 2.72 |
| AT4G11330 | 5.86 | 5.73 | 5.91 | 6.69 | 5.51 | 6.69 | 5.46 | 5.87 | 6.38 | 7.92 | 9.76 | 8.34 |
| AT4G30650 | 64.1 | 69.6 | 50.8 | 52.32 | 63.18 | 52.59 | 93.1 | 83.2 | 92.6 | 52.71 | 57.4 | 61.91 |
| AT4G31500 | 161 | 174 | 146 | 247.95 | 227.92 | 217.74 | 209 | 187 | 194 | 201.26 | 196.65 | 188.71 |
| AT4G39940 | 22.9 | 29.9 | 22.6 | 43.39 | 40.48 | 39.91 | 40.1 | 32.6 | 28.5 | 34.73 | 32.64 | 31.79 |
| AT5G10380 | 7.12 | 8.48 | 8.24 | 6.49 | 4.71 | 7.54 | 11.5 | 9.88 | 10.5 | 3.74 | 4.96 | 7.76 |
| AT5G38900 | 9.22 | 8.42 | 6.69 | 12.3 | 12.09 | 15.01 | 12.6 | 9.07 | 8.39 | 10.16 | 11.3 | 8.72 |
| AT5G45070 | 32.1 | 29.8 | 20.4 | 28.58 | 29.82 | 38.8 | 32.2 | 22.3 | 22.9 | 18.85 | 14.83 | 14.96 |
| AT5G54610 | 0.46 | 0.59 | 0 | 0.39 | 1.38 | 0.56 | 1.12 | 1.25 | 0.99 | 0.09 | 0.12 | 0.23 |

| GeneID | Annotation | | DEGs | | up_or_down | | log2FC | |
|---|---|---|---|---|---|---|---|---|
| | | | Ca | Cb | Ca | Cb | Ca | Cb |
| AT1G02930 | glutathione S-transferase 6 | Defense | FALSE | TRUE | | down | 0.32 | -1 |
| AT1G18590 | sulfotransferase 17 | Defense | TRUE | FALSE | up | | 0.71 | 0.03 |
| AT1G21250 | cell wall-associated kinase | Defense | FALSE | TRUE | | down | 0.15 | -1.3 |
| AT1G23740 | Oxidoreductase, zinc-binding dehydrogenase | Defense | FALSE | TRUE | | down | 0.36 | -0.83 |
| AT1G24100 | UDP-glucosyl transferase 74B1 | Defense | TRUE | FALSE | up | | 0.54 | 0.05 |
| AT1G52030 | myrosinase-binding protein 2 | Defense | FALSE | TRUE | | down | 0.21 | -2.6 |
| AT1G52040 | myrosinase-binding protein 1 | Defense | FALSE | TRUE | | down | 0.43 | -2.7 |
| AT1G72930 | toll/interleukin-1 receptor-like | Defense | FALSE | TRUE | | down | -0.06 | -0.8 |
| AT1G75040 | pathogenesis-related gene 5 | Defense | FALSE | TRUE | | down | 0.16 | -0.92 |
| AT2G02130 | low-molecular-weight cysteine-rich 68 | Defense | TRUE | FALSE | down | | -0.59 | -0.26 |
| AT2G14560 | Protein of unknown function (DUF567) | Defense | FALSE | TRUE | | down | 0.6 | -1.7 |
| AT2G14610 | pathogenesis-related gene 1 | Defense | FALSE | TRUE | | down | 2 | -4.4 |
| AT2G20610 | Tyrosine transaminase family protein | Defense | TRUE | FALSE | up | | 0.49 | 0.09 |
| AT2G25110 | stromal cell-derived factor 2-like protein | Defense | FALSE | TRUE | | down | 0.04 | -0.43 |
| AT2G29350 | senescence-associated gene 13 | Defense | FALSE | TRUE | | down | 0.1 | -2.2 |
| AT2G38860 | Class I glutamine amidotransferase-like superfamily | Defense | TRUE | FALSE | up | | 0.68 | 0.02 |
| AT2G38870 | Serine protease inhibitor, potato inhibitor I | Defense | FALSE | TRUE | | down | 0.1 | -0.56 |
| AT2G42530 | cold regulated 15b | Defense | FALSE | TRUE | | down | -0.01 | -2.9 |
| AT2G42540 | cold-regulated 15a | Defense | FALSE | TRUE | | down | -0.24 | -3.5 |

| GeneID | Annotation | Defense | DEGs Ca | DEGs Cb | up_or_down Ca | up_or_down Cb | log2FC Ca | log2FC Cb |
|---|---|---|---|---|---|---|---|---|
| AT2G46650 | cytochrome B5 isoform C | Defense | TRUE | FALSE | up | | 0.56 | 0.29 |
| AT3G04210 | Disease resistance protein (TIR-NBS class) | Defense | FALSE | TRUE | | down | 0.14 | -0.57 |
| AT3G09840 | cell division cycle 48 | Defense | FALSE | TRUE | | down | -0.09 | -0.27 |
| AT3G28740 | Cytochrome P450 superfamily protein | Defense | FALSE | TRUE | | up | 0.06 | 0.46 |
| AT3G28940 | AIG2-like (avirulence induced gene) family | Defense | TRUE | FALSE | up | | 0.43 | 0.09 |
| AT3G52960 | Thioredoxin superfamily protein | Defense | FALSE | TRUE | | down | 0.16 | -0.34 |
| AT3G60420 | Phosphoglycerate mutase family protein | Defense | FALSE | TRUE | | down | 0.14 | -1.4 |
| AT3G63380 | ATPase E1-E2 type family protein / haloacid | Defense | FALSE | TRUE | | down | 0.13 | -0.96 |
| AT4G08870 | Arginase/deacetylase superfamily protein | Defense | FALSE | TRUE | | down | 0.09 | -1.3 |
| AT4G11330 | MAP kinase 5 | Defense | FALSE | TRUE | | up | 0.075 | 0.52 |
| AT4G30650 | Low temperature and salt responsive protei | Defense | FALSE | TRUE | | down | -0.17 | -0.7 |
| AT4G31500 | cytochrome P450, family 83, subfamily B, p | Defense | TRUE | FALSE | up | | 0.48 | 0.09 |
| AT4G39940 | APS-kinase 2 | Defense | TRUE | FALSE | up | | 0.57 | -0.06 |
| AT5G10380 | RING/U-box superfamily protein | Defense | FALSE | TRUE | | down | -0.09 | -0.97 |
| AT5G38900 | Thioredoxin superfamily protein | Defense | TRUE | FALSE | up | | 0.66 | 0.09 |
| AT5G45070 | phloem protein 2-A8 | Defense | FALSE | TRUE | | down | 0.21 | -0.71 |
| AT5G54610 | ankyrin | Defense | FALSE | TRUE | | down | 1.1 | -2.9 |

FIG. 4D

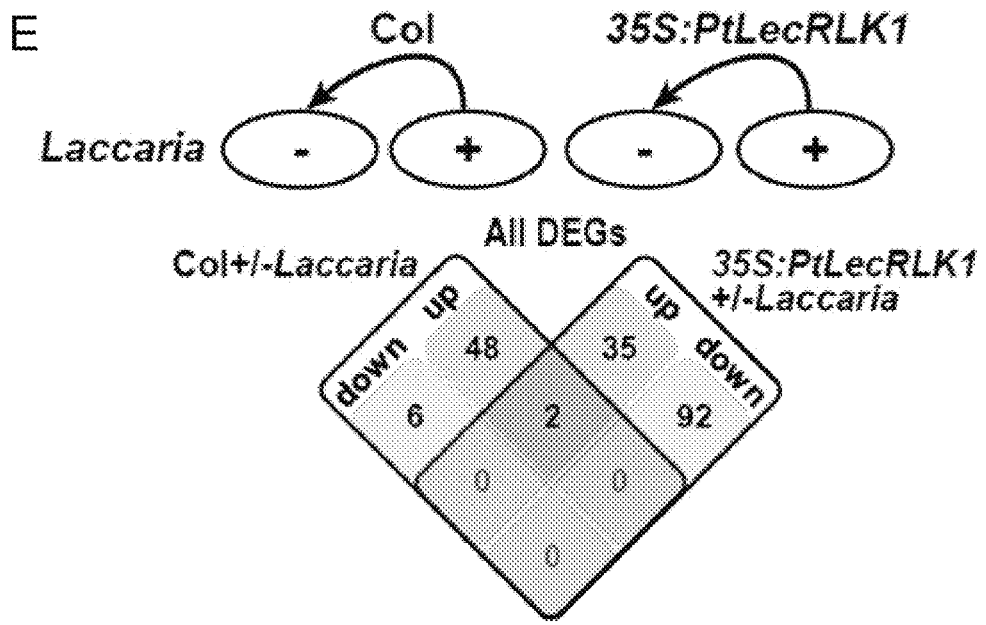
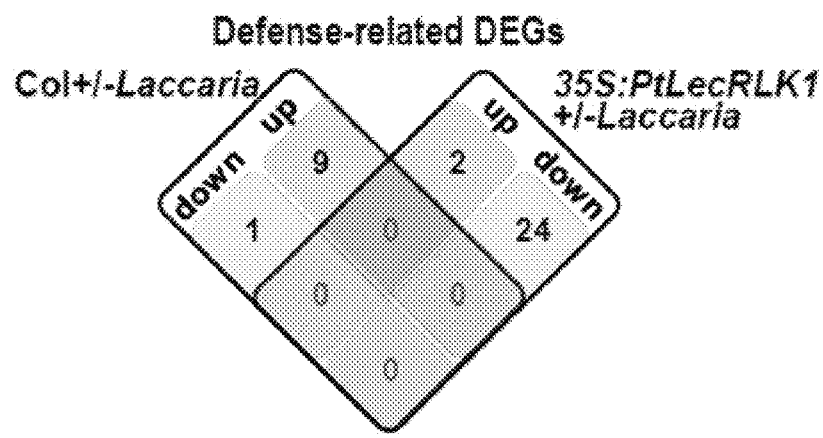
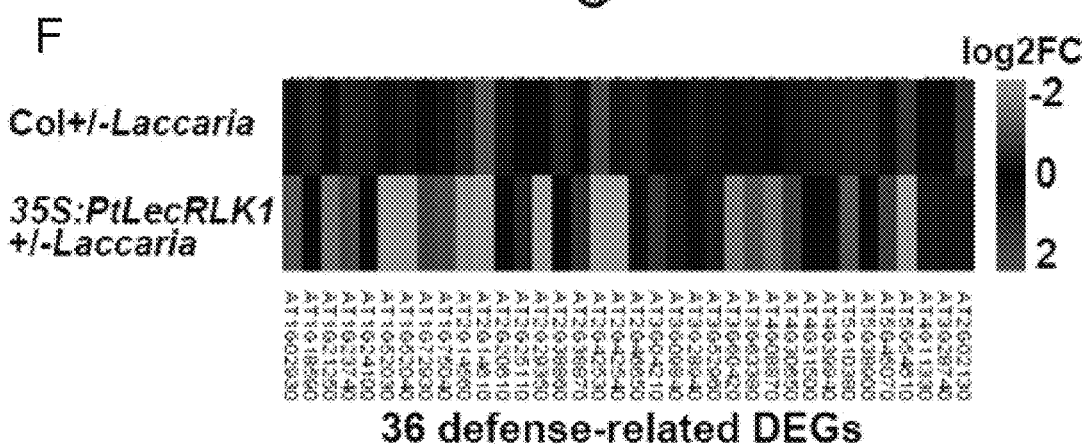
FIG. 4E – 4F

//(1)

SEQUENCE LISTING

```
<160> NUMBER OF SEQ ID NOS: 78

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide

<400> SEQUENCE: 1
tttctcactt tatgctggaa                                              20

<210> SEQ ID NO 2
<211> LENGTH: 25
<212> TYPE: DNA
<213> ORGANISM: Artificial Sequence
<220> FEATURE:
<223> OTHER INFORMATION: Oligonucleotide

<400> SEQUENCE: 2
tgctactttg atgatgtttt cttct                                        25

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide

<400> SEQUENCE: 3
atttcaaagc caccacctat                                              20

<210> SEQ ID NO 4
<211> LENGTH: 25
<212> TYPE: DNA
<213> ORGANISM: Artificial Sequence
<220> FEATURE:
<223> OTHER INFORMATION: Oligonucleotide
```

```
<400> SEQUENCE: 4
taacttccca cctagcaata caaga                                     25

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
gtgctccagt acaagaaaga                                           20

<210> SEQ ID NO 6
<211> LENGTH: 25
<212> TYPE: DNA
<213> ORGANISM: Artificial Sequence
<220> FEATURE:
<223> OTHER INFORMATION: Oligonucleotide

<400> SEQUENCE: 6
ctaagtgata gagcgcatac taata                                     25

<210> SEQ ID NO 7
<211> LENGTH: 21
<212> TYPE: DNA
<213> ORGANISM: Artificial Sequence
<220> FEATURE:
<223> OTHER INFORMATION: Oligonucleotide

<400> SEQUENCE: 7
tcgaacatcc aactgataca a                                         21

<210> SEQ ID NO 8
<211> LENGTH: 24
<212> TYPE: DNA
<213> ORGANISM: Artificial Sequence
<220> FEATURE:
<223> OTHER INFORMATION: Oligonucleotide

<400> SEQUENCE: 8
tcagattcct aaatgcatac gaaa                                      24

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide

<400> SEQUENCE: 9
caccaaacca actctgagtg aa                                        22

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide

<400> SEQUENCE: 10
ttacccaaca tcaaaactac attcg                                     25

<210> SEQ ID NO 11
<211> LENGTH: 27
```

```
<212> TYPE: DNA
<213> ORGANISM: Artificial Sequence
<220> FEATURE:
<223> OTHER INFORMATION: Oligonucleotide

<400> SEQUENCE: 11
gcacacttgg gttgtcagtg ttcaagc                                27

<210> SEQ ID NO 12
<211> LENGTH: 27
<212> TYPE: DNA
<213> ORGANISM: Artificial Sequence
<220> FEATURE:
<223> OTHER INFORMATION: Oligonucleotide

<400> SEQUENCE: 12
aattcattcc agctcttatc agattcc                                27

<210> SEQ ID NO 13
<211> LENGTH: 22
<212> TYPE: DNA
<213> ORGANISM: Artificial Sequence
<220> FEATURE:
<223> OTHER INFORMATION: Oligonucleotide

<400> SEQUENCE: 13
cttggactgg cactgtaatc gg                                     22

<210> SEQ ID NO 14
<211> LENGTH: 23
<212> TYPE: DNA
<213> ORGANISM: Artificial Sequence
<220> FEATURE:
<223> OTHER INFORMATION: Oligonucleotide

<400> SEQUENCE: 14
actgcttttg gtgatggact aac                                    23

<210> SEQ ID NO 15
<211> LENGTH: 28
<212> TYPE: DNA
<213> ORGANISM: Artificial Sequence
<220> FEATURE:
<223> OTHER INFORMATION: Oligonucleotide

<400> SEQUENCE: 15
caccaaaatg catttcattt ccatactt                               28

<210> SEQ ID NO 16
<211> LENGTH: 25
<212> TYPE: DNA
<213> ORGANISM: Artificial Sequence
<220> FEATURE:
<223> OTHER INFORMATION: Oligonucleotide

<400> SEQUENCE: 16
ttacccaaca tcaaaactac attcg                                  25

<210> SEQ ID NO 17
<211> LENGTH: 22
<212> TYPE: DNA
<213> ORGANISM: Artificial Sequence
<220> FEATURE:
<223> OTHER INFORMATION: Oligonucleotide

<400> SEQUENCE: 17
```
cccaacatca aaactacatt cg                                              22

<210> SEQ ID NO 18
<211> LENGTH: 23
<212> TYPE: DNA
<213> ORGANISM: Artificial Sequence
<220> FEATURE:
<223> OTHER INFORMATION: Oligonucleotide

<400> SEQUENCE: 18
gaaggaagac ctggaactac cat                                             23

<210> SEQ ID NO 19
<211> LENGTH: 23
<212> TYPE: DNA
<213> ORGANISM: Artificial Sequence
<220> FEATURE:
<223> OTHER INFORMATION: Oligonucleotide

<400> SEQUENCE: 19
tctcgaattc ctagaaagcc tct                                             23

<210> SEQ ID NO 20
<211> LENGTH: 22
<212> TYPE: DNA
<213> ORGANISM: Artificial Sequence
<220> FEATURE:
<223> OTHER INFORMATION: Oligonucleotide

<400> SEQUENCE: 20
gccttcgtgg tggttattaa gc                                              22

<210> SEQ ID NO 21
<211> LENGTH: 22
<212> TYPE: DNA
<213> ORGANISM: Artificial Sequence
<220> FEATURE:
<223> OTHER INFORMATION: Oligonucleotide

<400> SEQUENCE: 21
tccaacaatg gccagtaaac ac                                              22

<210> SEQ ID NO 22
<211> LENGTH: 21
<212> TYPE: DNA
<213> ORGANISM: Artificial Sequence
<220> FEATURE:
<223> OTHER INFORMATION: Oligonucleotide

<400> SEQUENCE: 22
atgaagatta aggtcgtggc a                                               21

<210> SEQ ID NO 23
<211> LENGTH: 20
<212> TYPE: DNA
<213> ORGANISM: Artificial Sequence
<220> FEATURE:
<223> OTHER INFORMATION: Oligonucleotide

<400> SEQUENCE: 23
tccgagtttg aagaggctac                                                 20

<210> SEQ ID NO 24
<211> LENGTH: 20
<212> TYPE: DNA
<213> ORGANISM: Artificial Sequence -continued

```
<220> FEATURE:
<223> OTHER INFORMATION: Oligonucleotide

<400> SEQUENCE: 24
atacacggag gatggacagg                                                    20

<210> SEQ ID NO 25
<211> LENGTH: 20
<212> TYPE: DNA
<213> ORGANISM: Artificial Sequence
<220> FEATURE:
<223> OTHER INFORMATION: Oligonucleotide

<400> SEQUENCE: 25
acatgcccaa gaaggttgag                                                    20

<210> SEQ ID NO 26
<211> LENGTH: 23
<212> TYPE: DNA
<213> ORGANISM: Artificial Sequence
<220> FEATURE:
<223> OTHER INFORMATION: Oligonucleotide

<400> SEQUENCE: 26
gctcagttca tagtccaaca aaa                                                23

<210> SEQ ID NO 27
<211> LENGTH: 24
<212> TYPE: DNA
<213> ORGANISM: Artificial Sequence
<220> FEATURE:
<223> OTHER INFORMATION: Oligonucleotide

<400> SEQUENCE: 27
tcagattcct aaatgcatac gaaa                                               24

<210> SEQ ID NO 28
<211> LENGTH: 20
<212> TYPE: DNA
<213> ORGANISM: Artificial Sequence
<220> FEATURE:
<223> OTHER INFORMATION: Oligonucleotide

<400> SEQUENCE: 28
atcattgttg ccatgggttt                                                    20

<210> SEQ ID NO 29
<211> LENGTH: 20
<212> TYPE: DNA
<213> ORGANISM: Artificial Sequence
<220> FEATURE:
<223> OTHER INFORMATION: Oligonucleotide

<400> SEQUENCE: 29
cacatgccaa ggtaccaaaa                                                    20

<210> SEQ ID NO 30
<211> LENGTH: 20
<212> TYPE: DNA
<213> ORGANISM: Artificial Sequence
<220> FEATURE:
<223> OTHER INFORMATION: Oligonucleotide

<400> SEQUENCE: 30
tgaaagccat ctccagaaca                                                    20
```

<210> SEQ ID NO 31
<211> LENGTH: 20
<212> TYPE: DNA
<213> ORGANISM: Artificial Sequence
<220> FEATURE:
<223> OTHER INFORMATION: Oligonucleotide

<400> SEQUENCE: 31
cccaaatcgg ttacttccaa                                               20

<210> SEQ ID NO 32
<211> LENGTH: 20
<212> TYPE: DNA
<213> ORGANISM: Artificial Sequence
<220> FEATURE:
<223> OTHER INFORMATION: Oligonucleotide

<400> SEQUENCE: 32
gatattcagg agggcgatca                                               20

<210> SEQ ID NO 33
<211> LENGTH: 20
<212> TYPE: DNA
<213> ORGANISM: Artificial Sequence
<220> FEATURE:
<223> OTHER INFORMATION: Oligonucleotide

<400> SEQUENCE: 33
cctagttttc ttgggcatcg                                               20

<210> SEQ ID NO 34
<211> LENGTH: 22
<212> TYPE: DNA
<213> ORGANISM: Artificial Sequence
<220> FEATURE:
<223> OTHER INFORMATION: Oligonucleotide

<400> SEQUENCE: 34
caatggactt tgacttggat ca                                            22

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide

<400> SEQUENCE: 35
gccacatttt cttcgtggtt                                               20

<210> SEQ ID NO 36
<211> LENGTH: 20
<212> TYPE: DNA
<213> ORGANISM: Artificial Sequence
<220> FEATURE:
<223> OTHER INFORMATION: Oligonucleotide

<400> SEQUENCE: 36
cgctactggt tcccgtgtat                                               20

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide

<400> SEQUENCE: 37
tcctgaagcc accaaagatt                                           20

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide

<400> SEQUENCE: 38
gagctgttgt gcctgtgtgt                                           20

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide

<400> SEQUENCE: 39
acgattgaag cgtgtgaatg                                           20

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide

<400> SEQUENCE: 40
ttgccaaaga gggttagcat                                           20

<210> SEQ ID NO 41
<211> LENGTH: 21
<212> TYPE: DNA
<213> ORGANISM: Artificial Sequence
<220> FEATURE:
<223> OTHER INFORMATION: Oligonucleotide

<400> SEQUENCE: 41
tttcattagg tgcagccatt a                                         21

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide

<400> SEQUENCE: 42
ctgctgaaca ctgccatgat                                           20

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide

<400> SEQUENCE: 43
ggagagcact gcctggatag                                           20

<210> SEQ ID NO 44

<211> LENGTH: 20
<212> TYPE: DNA
<213> ORGANISM: Artificial Sequence
<220> FEATURE:
<223> OTHER INFORMATION: Oligonucleotide

<400> SEQUENCE: 44
tctccagcaa aacctgccta                                               20

<210> SEQ ID NO 45
<211> LENGTH: 25
<212> TYPE: DNA
<213> ORGANISM: Artificial Sequence
<220> FEATURE:
<223> OTHER INFORMATION: Oligonucleotide

<400> SEQUENCE: 45
tgatcaaatg tagcactcta tccaa                                         25

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide

<400> SEQUENCE: 46
tatttggacg ctgacatgga                                               20

<210> SEQ ID NO 47
<211> LENGTH: 20
<212> TYPE: DNA
<213> ORGANISM: Artificial Sequence
<220> FEATURE:
<223> OTHER INFORMATION: Oligonucleotide

<400> SEQUENCE: 47
atggcgttca ctttgattgc                                               20

<210> SEQ ID NO 48
<211> LENGTH: 20
<212> TYPE: DNA
<213> ORGANISM: Artificial Sequence
<220> FEATURE:
<223> OTHER INFORMATION: Oligonucleotide

<400> SEQUENCE: 48
cgttgcgatt tacagcctaa                                               20

<210> SEQ ID NO 49
<211> LENGTH: 20
<212> TYPE: DNA
<213> ORGANISM: Artificial Sequence
<220> FEATURE:
<223> OTHER INFORMATION: Oligonucleotide

<400> SEQUENCE: 49
accctgttag gcatgctgtc                                               20

<210> SEQ ID NO 50
<211> LENGTH: 26
<212> TYPE: DNA
<213> ORGANISM: Artificial Sequence
<220> FEATURE:
<223> OTHER INFORMATION: Oligonucleotide

<400> SEQUENCE: 50
caacaaaagg gactttaatc taaaca                                          26

<210> SEQ ID NO 51
<211> LENGTH: 20
<212> TYPE: DNA
<213> ORGANISM: Artificial Sequence
<220> FEATURE:
<223> OTHER INFORMATION: Oligonucleotide

<400> SEQUENCE: 51
gaattgcccc atcctagaca                                                 20

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide

<400> SEQUENCE: 52
cggacgtctt cagttttggt                                                 20

<210> SEQ ID NO 53
<211> LENGTH: 20
<212> TYPE: DNA
<213> ORGANISM: Artificial Sequence
<220> FEATURE:
<223> OTHER INFORMATION: Oligonucleotide

<400> SEQUENCE: 53
gattgctcgt ggaatccttt                                                 20

<210> SEQ ID NO 54
<211> LENGTH: 22
<212> TYPE: DNA
<213> ORGANISM: Artificial Sequence
<220> FEATURE:
<223> OTHER INFORMATION: Oligonucleotide

<400> SEQUENCE: 54
caccaaacca actctgagtg aa                                              22

<210> SEQ ID NO 55
<211> LENGTH: 20
<212> TYPE: DNA
<213> ORGANISM: Artificial Sequence
<220> FEATURE:
<223> OTHER INFORMATION: Oligonucleotide

<400> SEQUENCE: 55
gcgtgcagga caatcaaata                                                 20

<210> SEQ ID NO 56
<211> LENGTH: 20
<212> TYPE: DNA
<213> ORGANISM: Artificial Sequence
<220> FEATURE:
<223> OTHER INFORMATION: Oligonucleotide

<400> SEQUENCE: 56
tggaagcagc aacagaaaaa                                                 20

<210> SEQ ID NO 57
<211> LENGTH: 20
<212> TYPE: DNA

<213> ORGANISM: Artificial Sequence
<220> FEATURE:
<223> OTHER INFORMATION: Oligonucleotide

<400> SEQUENCE: 57
taacggaagg ctcgaaagtg                                              20

<210> SEQ ID NO 58
<211> LENGTH: 22
<212> TYPE: DNA
<213> ORGANISM: Artificial Sequence
<220> FEATURE:
<223> OTHER INFORMATION: Oligonucleotide

<400> SEQUENCE: 58
tgtcttcgag ttgaaaccaa aa                                           22

<210> SEQ ID NO 59
<211> LENGTH: 19
<212> TYPE: DNA
<213> ORGANISM: Artificial Sequence
<220> FEATURE:
<223> OTHER INFORMATION: Oligonucleotide

<400> SEQUENCE: 59
atgaaaccca tgcccattc                                               19

<210> SEQ ID NO 60
<211> LENGTH: 20
<212> TYPE: DNA
<213> ORGANISM: Artificial Sequence
<220> FEATURE:
<223> OTHER INFORMATION: Oligonucleotide

<400> SEQUENCE: 60
cactgaaaag ccccaacatt                                              20

<210> SEQ ID NO 61
<211> LENGTH: 21
<212> TYPE: DNA
<213> ORGANISM: Artificial Sequence
<220> FEATURE:
<223> OTHER INFORMATION: Oligonucleotide

<400> SEQUENCE: 61
agaggatgat tctccaccaa a                                            21

<210> SEQ ID NO 62
<211> LENGTH: 22
<212> TYPE: DNA
<213> ORGANISM: Artificial Sequence
<220> FEATURE:
<223> OTHER INFORMATION: Oligonucleotide

<400> SEQUENCE: 62
tcgagagaga ctatttgcaa gc                                           22

<210> SEQ ID NO 63
<211> LENGTH: 20
<212> TYPE: DNA
<213> ORGANISM: Artificial Sequence
<220> FEATURE:
<223> OTHER INFORMATION: Oligonucleotide

<400> SEQUENCE: 63
ttgcacgagc agtagcattc                                              20

```
<210> SEQ ID NO 64
<211> LENGTH: 20
<212> TYPE: DNA
<213> ORGANISM: Artificial Sequence
<220> FEATURE:
<223> OTHER INFORMATION: Oligonucleotide

<400> SEQUENCE: 64
tccgtgatca aaacaatgga                                                   20

<210> SEQ ID NO 65
<211> LENGTH: 20
<212> TYPE: DNA
<213> ORGANISM: Artificial Sequence
<220> FEATURE:
<223> OTHER INFORMATION: Oligonucleotide

<400> SEQUENCE: 65
cccattaacc tgccattcac                                                   20

<210> SEQ ID NO 66
<211> LENGTH: 20
<212> TYPE: DNA
<213> ORGANISM: Artificial Sequence
<220> FEATURE:
<223> OTHER INFORMATION: Oligonucleotide

<400> SEQUENCE: 66
ctacgtgggg aaaatggatg                                                   20

<210> SEQ ID NO 67
<211> LENGTH: 20
<212> TYPE: DNA
<213> ORGANISM: Artificial Sequence
<220> FEATURE:
<223> OTHER INFORMATION: Oligonucleotide

<400> SEQUENCE: 67
tgcagcttct caaagcaatg                                                   20

<210> SEQ ID NO 68
<211> LENGTH: 20
<212> TYPE: DNA
<213> ORGANISM: Artificial Sequence
<220> FEATURE:
<223> OTHER INFORMATION: Oligonucleotide

<400> SEQUENCE: 68
acgaccgact ggagttgaat                                                   20

<210> SEQ ID NO 69
<211> LENGTH: 20
<212> TYPE: DNA
<213> ORGANISM: Artificial Sequence
<220> FEATURE:
<223> OTHER INFORMATION: Oligonucleotide

<400> SEQUENCE: 69
tgcccaagtt cttggttttc                                                   20

<210> SEQ ID NO 70
<211> LENGTH: 20
<212> TYPE: DNA
<213> ORGANISM: Artificial Sequence
<220> FEATURE:
```

<223> OTHER INFORMATION: Oligonucleotide

<400> SEQUENCE: 70
cctatcgagc atgggattgt                                                    20

<210> SEQ ID NO 71
<211> LENGTH: 19
<212> TYPE: DNA
<213> ORGANISM: Artificial Sequence
<220> FEATURE:
<223> OTHER INFORMATION: Oligonucleotide

<400> SEQUENCE: 71
cctttggggc cacaatgtt                                                     19

<210> SEQ ID NO 72
<211> LENGTH: 23
<212> TYPE: DNA
<213> ORGANISM: Artificial Sequence
<220> FEATURE:
<223> OTHER INFORMATION: Oligonucleotide

<400> SEQUENCE: 72
caaaagagag acaaggaagg aca                                                23

<210> SEQ ID NO 73
<211> LENGTH: 20
<212> TYPE: DNA
<213> ORGANISM: Artificial Sequence
<220> FEATURE:
<223> OTHER INFORMATION: Oligonucleotide

<400> SEQUENCE: 73
tcgttaaatg gcgagtacga                                                    20

<210> SEQ ID NO 74
<211> LENGTH: 22
<212> TYPE: DNA
<213> ORGANISM: Artificial Sequence
<220> FEATURE:
<223> OTHER INFORMATION: Oligonucleotide

<400> SEQUENCE: 74
tggaacttgc ctctagattt ga                                                 22

<210> SEQ ID NO 75
<211> LENGTH: 20
<212> TYPE: DNA
<213> ORGANISM: Artificial Sequence
<220> FEATURE:
<223> OTHER INFORMATION: Oligonucleotide

<400> SEQUENCE: 75
caacatcaaa cagctcgtga                                                    20

<210> SEQ ID NO 76
<211> LENGTH: 20
<212> TYPE: DNA
<213> ORGANISM: Artificial Sequence
<220> FEATURE:
<223> OTHER INFORMATION: Oligonucleotide

<400> SEQUENCE: 76
acctcgaccc aagcatgtta                                                    20

```
<210> SEQ ID NO 77
<211> LENGTH: 24
<212> TYPE: DNA
<213> ORGANISM: Artificial Sequence
<220> FEATURE:
<223> OTHER INFORMATION: Oligonucleotide

<400> SEQUENCE: 77
cctataaatt gtgaaatcca gctt                                              24

<210> SEQ ID NO 78
<211> LENGTH: 739
<212> TYPE: PRT
<213> ORGANISM: Populus tremula x Populus tremuloides

<400> SEQUENCE: 78
```

Met His Phe Ile Ser Ile Leu Leu Phe Cys Phe Phe Leu Leu Leu Asp
1               5                   10                  15

Arg Glu Val Ala Thr Ala Ile Asp Ile Ile Asn Thr Thr Gln Pro Ile
            20                  25                  30

Ile Asp Gly Asp Thr Met Val Ser Ala Asp Gly Thr Tyr Glu Leu Gly
        35                  40                  45

Phe Phe Ser Pro Ala Lys Ser Lys Asp Arg Tyr Leu Gly Ile Trp Tyr
    50                  55                  60

Gly Lys Ile Arg Val Gln Thr Val Trp Val Ala Asn Arg Glu Thr
65                  70                  75                  80

Pro Leu Asn Asp Ser Ser Gly Val Leu Arg Leu Thr Asn Lys Gly Ile
                85                  90                  95

Leu Ile Ile Leu Asp Arg His Lys Ser Val Ile Trp Ser Ser Ile Thr
            100                 105                 110

Thr Arg Pro Ala Arg Asn Pro Thr Ala Gln Leu Leu Asp Ser Gly Asn
        115                 120                 125

Leu Val Val Lys Glu Glu Gly Asp Ser Asn Leu Glu Asn Ser Leu Trp
    130                 135                 140

Gln Ser Phe Glu His Pro Thr Asp Thr Ile Leu Ala Asp Met Lys Ile
145                 150                 155                 160

Gly Trp Asn Arg Ile Ala Gly Met Asn Leu Tyr Leu Thr Ser Trp Lys
                165                 170                 175

Ser Ala Asp Asp Pro Ser Arg Gly Asn Phe Thr Cys Met Met Val Pro
            180                 185                 190

Tyr Gly Tyr Pro Glu Ile Val Leu Thr Glu Gly Ser Lys Val Lys Cys
        195                 200                 205

Arg Ser Gly Ala Trp Asn Gly Ile Leu Leu Ser Gly Leu Thr Gln Leu
    210                 215                 220

Lys Ser Thr Ser Lys Phe Thr Ile Glu Phe Leu Phe Asn Glu Lys Glu
225                 230                 235                 240

Met Phe Leu Thr Tyr His Phe His Ser Ser Ile Leu Ser Arg Ala
                245                 250                 255

Val Val Ser Pro Asn Gly Asp Phe Gln Glu Phe Val Leu Asn Glu Lys
            260                 265                 270

Thr Gln Ser Trp Phe Leu Tyr Asp Thr Gly Thr Thr Asp Asn Cys Asp
        275                 280                 285

Arg Tyr Ala Leu Cys Gly Thr Asn Gly Ile Cys Ser Ile Asp Ser Ser
    290                 295                 300

Pro Val Leu Cys Asp Cys Leu Asp Gly Phe Val Pro Lys Thr Pro Arg
305                 310                 315                 320

```
Asp Trp Asn Val Ala Asp Trp Ser Asn Gly Cys Val Arg Arg Thr Pro
                325                 330                 335

Leu Asn Cys Ser Gly Asp Gly Phe Gln Lys Leu Ser Gly Leu Lys Leu
            340                 345                 350

Pro Glu Thr Lys Thr Ser Trp Phe Asn Thr Ser Met Asn Leu Glu Glu
        355                 360                 365

Cys Lys Lys Cys Ile Lys Asn Cys Ser Cys Thr Ala Tyr Ser Asn
    370                 375                 380

Leu Asp Ile Arg Asn Gly Gly Ser Gly Cys Leu Leu Trp Phe Gly Asp
385                 390                 395                 400

Leu Ile Asp Ile Arg Val Ile Ala Val Asn Glu Gln Asp Val Tyr Ile
                405                 410                 415

Arg Met Ala Glu Ser Glu Leu Asp Asn Gly Asp Gly Ala Lys Ile Asn
                420                 425                 430

Thr Lys Ser Asn Ala Lys Lys Arg Ile Ile Ser Thr Ala Leu Phe
            435                 440                 445

Thr Gly Ile Leu Phe Leu Gly Leu Ala Leu Val Leu Tyr Ile Trp Lys
        450                 455                 460

Gln Gln Gln Lys Asn Arg Gln Ser Asn Asn Met Arg Lys Lys Glu Asp
465                 470                 475                 480

Leu Glu Leu Pro Phe Phe Asp Phe Gly Thr Leu Ala Cys Ala Thr Asn
                485                 490                 495

Asn Phe Ser Thr Asp Asn Lys Leu Gly Glu Gly Gly Phe Gly Pro Val
            500                 505                 510

Tyr Lys Gly Thr Leu Ala Asp Gly Arg Glu Ile Ala Val Lys Arg Leu
        515                 520                 525

Ser Arg Asn Ser Arg Gln Gly Leu Asp Glu Leu Lys Asn Glu Ala Asn
    530                 535                 540

Tyr Ile Val Lys Leu Gln His Arg Asn Leu Val Lys Leu Leu Gly Cys
545                 550                 555                 560

Cys Ile Glu Gly Asp Glu Lys Met Leu Ile Tyr Glu Phe Leu Pro Asn
                565                 570                 575

Lys Ser Leu Asp Val Leu Ile Phe Glu Lys Thr His Ser Leu Gln Leu
            580                 585                 590

Asp Trp Pro Lys Arg Tyr Lys Ile Ile Asn Gly Ile Ala Arg Gly Ile
        595                 600                 605

Leu Tyr Leu His Gln Asp Ser Arg Leu Arg Val Ile His Arg Asp Leu
    610                 615                 620

Lys Ala Ser Asn Ile Leu Leu Asp Tyr Glu Leu Ser Pro Lys Ile Ser
625                 630                 635                 640

Asp Phe Gly Leu Ala Arg Ser Phe Gly Gly Asn Glu Thr Glu Ala Asn
                645                 650                 655

Thr Asn Lys Val Ala Gly Thr Phe Gly Tyr Ile Ser Pro Glu Tyr Ala
            660                 665                 670

Asn Tyr Gly Leu Tyr Ser Leu Asn Ser Asp Val Phe Ser Phe Gly Val
        675                 680                 685

Leu Val Leu Glu Ile Val Ser Gly Lys Arg Asn Arg Gly Phe Cys His
    690                 695                 700

Pro Asp His His Leu Asn Leu Leu Gly His Ala Trp Lys Leu Phe Lys
705                 710                 715                 720
```

```
Glu Asn Arg Arg Ser Arg Arg Gln Ala Lys His Val Glu Cys Ser Phe
            725                 730                 735
Asp Val Gly
```

METHODS OF IMPROVING MYCORRHIZATION IN PLANTS AND GENETICALLY MODIFED PLANTS WITH IMPROVED MYCORRHIZATION

CROSS REFERENCE TO RELATED APPLICATION

This application claims the benefit of priority from U.S. Provisional Application No. 62/703,934, filed Jul. 27, 2018, the entire contents of which are incorporated herein by reference.

STATEMENT REGARDING FEDERALLY SPONSORED RESEARCH OR DEVELOPMENT

This disclosure was made with government support under a research project supported by Prime Contract No. DE-AC05-00OR22725 awarded by the U.S. Department of Energy. The government has certain rights in this invention.

INCORPORATION BY REFERENCE OF SEQUENCE LISTING

The Sequence Listing in an ASCII text file, named as 37197_SEQ_ST25.txt of 21 KB, created on May 1, 2019, and submitted to the United States Patent and Trademark Office via EFS-Web, is incorporated herein by reference.

BACKGROUND

*Populus* species, as keystone members of boreal and temperate ecosystems (Whitham, T. G. et al., *Science* 320, 492-495 (2008)), interact with a wide variety of microbes (Vozzo, J. A., Hacskaylo, E., *Bull. Torrey Bot. Club* 101, 182-186 (1974), Gottel, N. R. et al., *Appl. Environ. Microbiol.* 77, 5934-5944 (2011)). The *Populus-Laccaria bicolor* system has emerged as an excellent system of choice for studying plant-ectomycorrhizal interactions aided by the availability of both *Populus* and *Laccaria* reference genomes and genetic tools (Tuskan, G. A. et al., *Science* 313, 1596-1604 (2006), Martin, F. et al., *Nature* 452, 88-92 (2008)). Modes of action and molecular mechanisms underlying ectomycorrhizal interactions are poorly understood in this and all other plant-mycorrhizal systems though progress has been made in recent years (Martin, F., et al., *Nat. Rev. Microbiol.* 14, 760-773 (2016)). Active recruitment and acceptance of mycorrhization have been proposed to occur in a species-specific manner (Kohler, A. et al., *Nat. Genet.* 47, 410-415 (2015)) and *L. bicolor* has been found to preferentially colonize *P. trichocarpa* over *P. deltoides* (Tagu, D. et al., *Mycorrhiza* 10, 237-240 (2001), Labbé, J. et al., *Tree Genet. Genomes* 7, 617-627 (2011)).

Mycorrhizal symbiosis represent the most widespread plant-microbe association which offers numerous benefits including (1) enhancing carbon sequestration in terrestrial ecosystems, (2) increasing nutrient availability to host plants, (3) remediating degraded soils, and (4) improving water use efficiency. All of these beneficial aspects make mycorrhizal association an excellent strategy for improving the sustainable production of long-lived perennial bioenergy, lumber, and pulp and paper feedstocks. One such economically important perennial forestry crop is *Populus*, a widely used cellulosic biofuels, lumber, and pulp and paper feedstocks which is a host to a wide variety of microbial symbionts found within roots as endophytes or externally as ectomycorrhiza. The *Populus-Laccaria* mycorrhizal symbiosis is one such interaction that has immense potential for enhancing plant productivity in marginal environments. In *Populus*, colonization by the symbiont *Laccaria bicolor* can lead to doubling of the biomass yield. Studies have demonstrated the species-specificity of this interaction, with *Laccaria*, a basidiomycete, preferentially colonizing *P. trichocarpa* over *P. deltoides* (Tagu, D. et al., *Mycorrhiza* 10, 237-240 (2001), Labbé, J. et al., *Tree Genet. Genomes* 7, 617-627 (2011)). Prior to this disclosure, no specific host-derived genetic determinants have been identified to explain *Laccaria*'s species preference.

SUMMARY OF THE DISCLOSURE

One aspect of this disclosure provides a method for improving mycorrhization in a plant or plant cell, comprising expressing an exogenous nucleic acid encoding a LecRLK1 variant or homolog in the plant or plant cell.

In some embodiments, the LecRLK1 variant or homolog is a *P. trichocarpa* LecRLK1 (PtLecRLK1) variant or homolog. In some embodiments, the PtLecRLK1 variant or homolog comprises an amino acid sequence shown by SEQ ID NO: 78.

In some embodiments, the exogenous nucleic acid encoding LecRLK1 is stably transfected or transformed into the plant genome.

In some embodiments, the exogenous nucleic acid encoding LecRLK1 is expressed in the root tissue of the plant. In some embodiments, the root-specific expression is achieved by a root-specific promoter selected from the group consisting of DR5, PtrDP3 and PtrMX3.

In some embodiments, the plant is selected from the group consisting of genera *Allium, Arabidopsis, Brassica, Capsicum, Citrullus, Cucumis, Eucalyptus, Fragaria, Glycine, Gossypium, Hordeurn, Ipomoea, Malus, Manihot, Nicotiana, Oryza, Populus, Prunus, Rosa, Solanum, Spinacia, Triticum, Panicum, Saccharum, Setaria, Sorghum, Zea, Kalanchoe Phalaenopsis, Ananas* and *Crassula*.

Another aspect of this disclosure is directed to a genetically modified plant or plant cell comprising an exogenous nucleic acid encoding a LecRLK1 variant or homolog in the plant or plant cell, and wherein the LecRLK1 variant or homolog is expressed in the plant or plant cell.

In some embodiments, the LecRLK1 variant or homolog is a *P. trichocarpa* LecRLK1 (PtLecRLK1) variant or homolog. In some embodiments, the PtLecRLK1 variant or homolog comprises an amino acid sequence shown by SEQ ID NO: 78.

In some embodiments, the exogenous nucleic acid is stably transfected or transformed into the plant genome. In a specific embodiment, the exogenous nucleic acid is expressed in the root tissue of the plant.

Another aspect of the disclosure is directed to an expression vector comprising a nucleotide sequence encoding a LecRLK1 allelic variant or homolog operably linked to a regulatory region that is functional in a plant or plant cell.

In some embodiments, the LecRLK1 variant or homolog is a *P. trichocarpa* LecRLK1 (PtLecRLK1) variant or homolog. In some embodiments, the PtLecRLK1 variant or homolog comprises an amino acid sequence shown by SEQ ID NO: 78.

In some embodiments, the regulatory region of the expression vector comprises a promoter selected from the group consisting of a constitutive promoter, a tissue-specific promoter, and a regulated promoter.

In some embodiments, the tissue-specific promoter is a root-specific promoter. In some embodiments, the root-specific promoter is selected from the group consisting of DR5, PtrDP3 and PtrMX3.

In some embodiments, the constitutive promoter is selected from the group consisting of a ubiquitin promoter, a cauliflower mosaic virus (CaMV) 35S promoter, a nopaline synthase (nos) promoter, an actin promoter, a peanut chlorotic streak caulimovirus promoter, a *Chlorella* virus methyltransferase gene promoter, a full-length transcript promoter form figwort mosaic virus, a pEMU promoter, a MAS promoter, a maize H3 histone promoter and an *Agrobacterium* gene promoter.

In some embodiments, the regulated promoter is selected from the group consisting of a stress induced promoter, a chemical-induced promoter, a light induced promoter, a dark-induced promoter, and a circadian-clock controlled promoter.

Another aspect of this disclosure is directed to a method for improving mycorrhization in a plant or plant cell, comprising introducing an expression vector comprising a nucleotide sequence encoding a LecRLK1 allelic variant or homolog operably linked to a regulatory region that is functional in a plant or plant cell into a plant or plant cell, and expressing the nucleotide sequence in the plant or plant cell.

Another aspect of this disclosure is directed to a plant or plant cell comprising an expression vector comprising a nucleotide sequence encoding a LecRLK1 allelic variant or homolog operably linked to a regulatory region that is functional in a plant or plant cell.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 4A-4F. (A)-(D) Transcriptomic analysis of differentially expressed genes in *Arabidopsis* plants co-cultivated with *L. bicolor*. "All.DEGs", all differentially expressed genes in Col-0 and 35S:PtLecRLK1 transgenic plants. (E) Transcriptomics analysis of defense-related genes in the wild-type Col-0 and 35S:PtLecRLK1 transgenic plants (line #8) co-cultivated with *L. bicolor*. "DEG" refer to "differentially expressed genes" (p<0.05). (F) Defense-related differentially expressed gene (DEG) expressions shown as clusters.

DETAILED DESCRIPTION

Definitions

Figure 1:
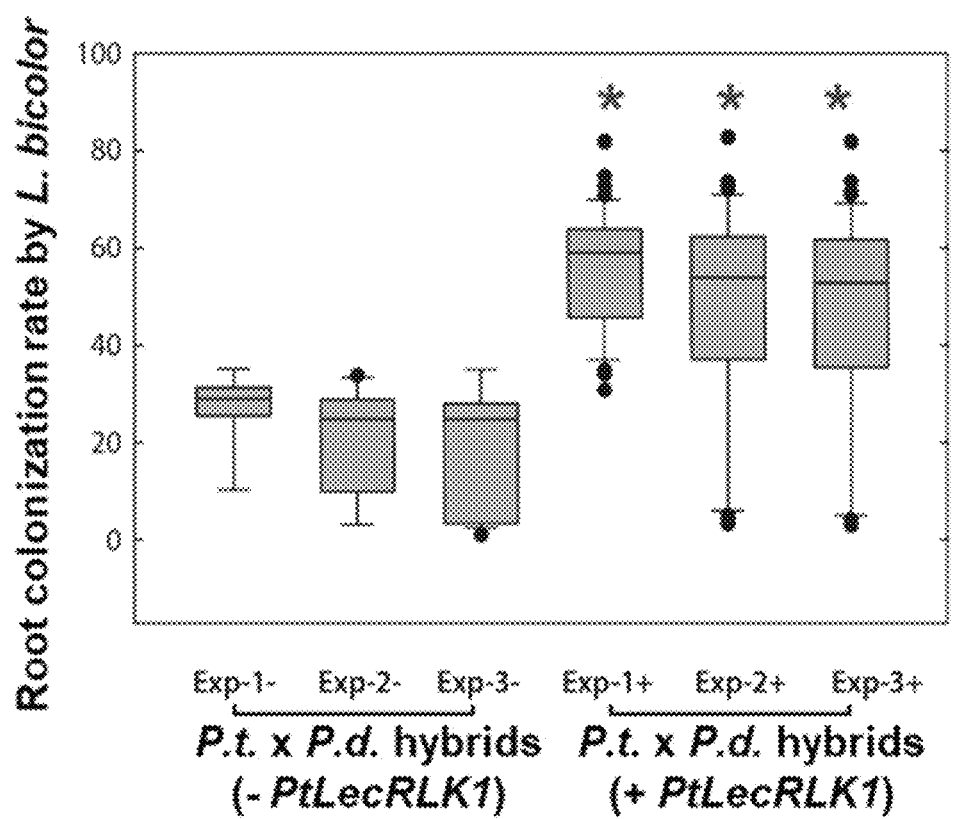
FIG. 1. Root colonization rate by *L. bicolor* evaluated among *P. trichocarpa* (P.t.) x *P. deltoides* (P. d.) hybrids with (−) or without deletion (+) of the PtLecRLK1 locus. "Exp−" refers to three independent experiments. * means that the result is significantly different from genotypes with PtLecRLK1 deletion as determined by ANOVA (p<0.05) with a minimum of 72 genotypes in each experiment.

Unless defined otherwise, all technical and scientific terms used herein have the same meaning as commonly understood by one of ordinary skill in the art to which this invention belongs.

As used herein, the term "about" refers to an approximately +/−10% variation from a given value.

The term "exogenous," as used herein, refers to a substance or molecule originating or produced outside of an organism. The term "exogenous gene" or "exogenous nucleic acid molecule," as used herein, refers to a nucleic acid that codes for the expression of an RNA and/or protein that has been introduced ("transformed") into a cell or a progenitor of the cell. An exogenous gene may be from a different species (and so a "heterologous" gene) or from the same species (and so a "homologous" gene), relative to the cell being transformed. A transformed cell may be referred to as a recombinant or genetically modified cell. An "endogenous" nucleic acid molecule, gene, or protein can represent the organism's own gene or protein as it is naturally produced by the organism.

The term "expression" refers to the process of converting genetic information of a polynucleotide into RNA through transcription, which is catalyzed by an enzyme, RNA polymerase and into protein, through translation of mRNA on ribosomes. Expression can be, for example, constitutive or regulated, such as, by an inducible promoter (e.g., lac operon, which can be triggered by Isopropyl β-D-1-thiogalactopyranoside (IPTG)). Up-regulation or overexpression refers to regulation that increases the production of expression products (mRNA, polypeptide or both) relative to basal or native states, while inhibition or down-regulation refers to regulation that decreases production of expression products (mRNA, polypeptide or both) relative to basal or native states. Expression of a gene can be measured through a suitable assay, such as real-time quantitative reverse transcription polymerase chain reaction (qRT-PCR), Northern blot, transcriptome sequencing and Western blot.

The term "gene," as used herein, refers to a segment of nucleic acid that encodes an individual protein or RNA and can include both exons and introns together with associated regulatory regions such as promoters, operators, terminators, 5' untranslated regions, 3' untranslated regions, and the like.

The term "genetically modified" (or "genetically engineered" or "transgenic" or "cisgenic") refers to a plant comprising a manipulated genome or nucleic acids. In some embodiments, the manipulation is the addition of exogenous nucleic acids to the plant. In some embodiments, the manipulation is changing the endogenous genes of the plant.

The term "homologous" refers to nucleic acids or polypeptides that are highly related at the level of nucleotide or amino acid sequence. Nucleic acids or polypeptides that are homologous to each other are termed "homologues." The term "homolog" refers to a gene related to a second gene by descent from a common ancestral DNA sequence, therefore, the corresponding polynucleotide/polypeptide has a certain degree of homology, that is to say sequence identity (at least 40%, 60%, 65%, 66%, 68%, 70%, 75%, 80%, 86%, 88%, 90%, 92%, 95%, 97% or 99% identity).

The term mycorrhization refers to formation of mycorrhiza on the roots of a plant. The term "mycorrhiza" refers to a symbiotic association of the mycelium (the vegetative part of a fungus) of certain fungi with the root cells of some vascular plants.

In some embodiments, mycorrhization of a plant comprises a symbiotic relation of the plant with a fungus from the family Hydnangiaceae. In a specific embodiment the fungus from the family Hydnangiaceae is *Zaccaria bicolor*.

In some embodiments, mycorrhization of a plant comprises a symbiotic relation of the plant with a fungus from the family Sebacinales. In a specific embodiment the fungus from the family Sebacinales is *Serendipita indica*.

In some embodiments, mycorrhization of a plant comprises a symbiotic relation of the plant with a fungus from the family Hymenogastraceae. In a specific embodiment the fungus from the family Hymenogastraceae is from the genus *Hebeloma*.

As used herein, the term "nucleic acid" has its general meaning in the art and refers to refers to a coding or non-coding nucleic sequence. Nucleic acids include DNA (deoxyribonucleic acid) and RNA (ribonucleic acid) nucleic acids. Examples of nucleic acid thus include but are not limited to DNA, mRNA, tRNA, rRNA, tmRNA, miRNA, piRNA, snoRNA, and snRNA. Nucleic acids thus encompass coding and non-coding region of a genome (i.e. nuclear or mitochondrial or chloroplast).

The term "operably linked" refers to positioning of a regulatory region and a sequence to be transcribed in a nucleic acid so as to influence transcription or translation of such a sequence. For example, to bring a coding sequence under the control of a regulatory region, the translation initiation site of the translational reading frame of the polypeptide is typically positioned between one and about fifty nucleotides downstream of the promoter. A regulatory region can, however, be positioned as much as about 5,000 nucleotides upstream of the translation initiation site or about 2,000 nucleotides upstream of the transcription start site. A regulatory region typically comprises at least a core (basal) promoter.

The term "regulatory region" refers to a nucleic acid having nucleotide sequences that influence transcription or translation initiation and rate and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns and combinations thereof.

A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., *The Plant Cell*, 1:977-984 (1989)). The choice of regulatory regions to be included depends upon several factors, including, but not limited to, efficiency, selectability, inducibility, desired expression level and cell- or tissue-preferential expression. It is a routine matter for one of skill in the art to modulate the expression of a coding sequence by appropriately selecting and positioning regulatory regions relative to the coding sequence.

As used herein, the term "variant" refers to alternative forms of a gene, genetic locus, gene sequence or amino acid sequence encoded by the gene, genetic locus or gene sequence. Each variant, as used for polynucleotides, has a distinct nucleic acid sequence at the locus of interest. Each variant, as used for polypeptides, has a distinct amino acid at the amino acid position of interest. A variant of a gene or DNA sequence can show a sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the reference sequence (prototype) of said gene. Sequence identity for polynucleotides refers to the percent of exact matches between the nucleic acids of two sequences which are being compared. A variant of a polypeptide can show a sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the reference sequence (prototype) of said polypeptide. Sequence identity for polypeptides refers to the percent of exact matches between the amino acids of two sequences which are being compared.

A "vector" is a replicon, such as a plasmid, phage or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses and retroviruses. Numerous vectors and expression systems are commercially available from such corporations as Novagen (Madison, Wis.), Clontech (Mountain View, Calif.), Stratagene (La Jolla, Calif.) and Invitrogen/Life Technologies (Carlsbad, Calif.).

GENERAL DESCRIPTION

Plants

There is no specific limitation on the plants that can be used in the methods of the present disclosure, as long as the plant is suitable to be transformed by a gene. The term "plant," as used herein, includes whole plants, plant tissues or plant cells. The plants that can be used for the methods and compositions of the present disclosure include various crops, flower plants or plants of forestry, etc. Specifically, the plants include, but are not limited to, dicotyledon, monocotyledon or gymnosperm. More specifically, the plants include, but is not limited to, wheat, barley, rye, rice, corn, sorghum, beet, apple, pear, plum, peach, apricot, cherry, strawberry, *Rubus swinhoei* Hance, blackberry, bean, lentil, pea, soy, rape, mustard, opium poppy, *olea europea*, *helianthus*, coconut, plant producing castor oil, cacao, peanut, calabash, cucumber, watermelon, cotton, flax, *cannabis*, jute, citrus, lemon, grapefruit, spinach, lettuce, asparagus, cabbage, *Brassica campestris* L. ssp. *Pekinensis, Brassica campestris* L. ssp. *chinensis*, carrot, onion, murphy, tomato, green pepper, avocado, *cassia*, camphor, tobacco, nut, coffee, eggplant, sugar cane, tea, pepper, grapevine, nettle grass, banana, natural rubber tree and ornamental plant, etc.

In some embodiment the methods and compositions of the present disclosure are also be used over a broad range of plant species from the dicot genera *Acer, Afzelia, Arabidopsis, Betula, Brassica, Eucalyptus, Fagus, Fraxinus, Glycine,*

*Gossypium, Jatropha, Juglans, Linum, Lycopersicon, Medicago, Micropus, Populus, Prunus, Quercus, Salix, Solanum, Tectona* and *Trifolium*; and the monocot genera *Agrostis, Avena, Festuca, Hordeum, Lemna, Lolium, Milium, Miscanthus, Oryza, Panicum, Pennisetum, Phalaris, Phleum, Poa, Saccharum, Secale, Sorghum, Triticum, Zea* and *Zoysia*; and the gymnosperm genera *Abies, Picea* and *Pinus*. In some embodiments, a plant is a member of the species *Festuca arundinacea, Miscanthus* hybrid (*Miscanthus x giganteus*), *Miscanthus sinensis, Miscanthus sacchariflorus, Panicum virgatum, Pennisetum purpureum, Phalaris arundinacea, Populus* spp including but not limited to *balsamifera, deltoides, tremuloides, tremula*, alba and *maximowiczii, Saccharum* spp., *Secale cereale, Sorghum almum, Sorghum halcapense* or *Sorghum vulgare*. In certain embodiments, the polynucleotides and vectors described herein can be used to transform a number of monocotyledonous and dicotyledonous plants and plant cell systems, wherein such plants are hybrids of different species.

In some embodiments, the plant for the methods and compositions of the present disclosure is a C3 plant. In some embodiment, the C3 plant is selected from the group consisting of genera *Allium, Arabidopsis, Brassica, Capsicum, Citrullus, Cucumis, Eucalyptus, Fragaria, Glycine, Gossypium, Hordeum, Ipomoea, Malus, Manihot, Nicotiana, Oryza, Populus, Prunus, Rosa, Solanum, Spinacia* and *Triticum*.

In some embodiments, the plant for the methods and compositions of the present disclosure is a C4 plant. In some embodiment, the C4 plant is selected from the group consisting of genera *Panicum, Saccharum, Setaria, Sorghum* and *Zea*.

Methods of Improving Mychorrization

The present disclosure describes a process of improving mycorrhization in plants. In some embodiment, mycorrhization is improved at least 20%, 25%, 30%, 35%, 40%, 45% 50%, 55%, 60%, 65%, 70%, 75%, 80%, 85%, 90%, 95%, 100%, 150%, 200%, 300%, 400%, or 500% as compared to a control plant. The term "control plant" as used herein refers to a plant cell, an explant, seed, plant component, plant tissue, plant organ, or whole plant used to compare against transgenic or genetically-modified plant for the purpose of identifying an enhanced phenotype or a desirable trait in the transgenic or genetically modified plant. A "control plant" may in some cases be a transgenic plant line that comprises an empty vector or marker gene, but does not contain the recombinant polynucleotide of interest that is present in the transgenic or genetically modified plant being evaluated. A control plant may be a plant of the same line or variety as the transgenic or genetically modified plant being tested, or it may be another line or variety, such as a plant known to have a specific phenotype, characteristic, or known genotype. A suitable control plant would include a genetically unaltered or non-transgenic plant of the parental line used to generate a transgenic plant herein.

With methods of this disclosure, it is possible to generate plants which have more mychrorization, primarily in their root tissues. These improved plants produce more biomass, and/or more crop and plant product derived thereof, if grown under conditions of low water availability/drought or poor soil conditions in comparison with plants not subjected to the method according to the present disclosure. In some embodiments, the biomass of the plant produced by the methods of the instant disclosure is increased by at least 5%, by at least 10%, by at least 15%, by at least 20%, or by at least 30% when compared to a corresponding control plant.

In some embodiments, the method of improving mychorrization in plant roots comprises expressing an exogenous nucleic acid encoding a LecRLK1 variant or homolog in a plant or plant cell. In some embodiments, the LecRLK1 variant or homolog is a *P. trichocarpa* LecRLK1 (PtLecRLK1) variant or homolog. In a specific embodiment, the PtLecRLK1 comprises an amino acid sequence shown by SEQ ID NO: 78. In a specific embodiment, the exogenous nucleic acid encoding LecRLK1 is stably transfected or transformed into the plant genome. In some embodiments, the exogenous nucleic acid encoding LecRLK1 is expressed in the root tissue of the plant.

Expression Vectors

The expression vectors described herein can be used to increase the expression of LecRLK1 in plants and enhance mycorrhization.

In some embodiments, the vector comprises a nucleic acid sequence encoding for a LecRLK1 variant or homolog. In some embodiments, the LecRLK1 variant or homolog is from a *Populus* species. In a specific embodiment, the *Populus* species is *Populus trichocarpa*, and the *P. trichocarpa* LecRLK1 (PtLecRLK1) comprises the sequence shown by SEQ ID NO: 78.

The vectors provided herein can include origins of replication, scaffold attachment regions (SARs) and/or markers. A marker gene can confer a selectable phenotype on a plant cell. For example, a marker can confer biocide resistance, such as resistance to an antibiotic (e.g., kanamycin, G418, bleomycin or hygromycin) or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin or Flag-tag (Kodak, New Haven, Conn.) sequences typically are expressed as a fusion with the encoded polypeptide. Such tags can be inserted anywhere within the polypeptide, including at either the carboxyl or amino terminus. As described herein, plant cells can be transformed with a recombinant nucleic acid construct to express a polypeptide of interest.

A variety of promoters are available for use, depending on the degree of expression desired. For example, a broadly expressing promoter promotes transcription in many, but not necessarily all, plant tissues. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter and ubiquitin promoters such as the maize ubiquitin-1 promoter.

In some embodiments, the promoter to drive expression of genes of interest is a constitutive promoter. In some embodiments the constitutive promoter is selected from the group consisting of a ubiquitin promoter, a cauliflower mosaic virus (CaMV) 35S promoter, an actin promoter, a peanut chlorotic streak caulimovirus promoter, a *Chlorella* virus methyltransferase gene promoter, a full-length transcript promoter form figwort mosaic virus, a pEMU promoter, a MAS promoter, a maize H3 histone promoter and an *Agrobacterium* gene promoter.

In some embodiments, the promoter to drive expression of genes of interest is a regulated promoter. In some embodiments the regulated promoter is selected from the group consisting of a stress induced promoter, chemical-induced promoter, a light induced promoter, a dark-induced promoter, and a circadian-clock controlled promoter.

Some suitable regulatory regions initiate transcription, only or predominantly, in certain cell types. For instance, promoters active in root tissue confer transcription in the roots of plants. Examples of such promoters include DR5, PtrDP3 and Ptr MX3.

In some embodiments, promoters of the instant application comprise inducible promoters. Inducible promoters confer transcription in response to external stimuli such as chemical agents or environmental stimuli. For example, inducible promoters can confer transcription in response to hormones such as gibberellic acid or ethylene or in response to light, nitrogen, shade or drought.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

A 5' untranslated region (UTR) can be included in nucleic acid constructs described herein. A 5' UTR is transcribed, but is not translated and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a vector, e.g., introns, enhancers, upstream activation regions, transcription terminators and inducible elements. Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

Techniques for introducing nucleic acids into monocotyledonous and dicotyledonous plants are known in the art and include, without limitation, *Agrobacterium*-mediated transformation, viral vector-mediated transformation, electroporation and particle gun transformation, e.g., U.S. Pat. Nos. 5,538,880, 5,204,253, 6,329,571 and 6,013,863. If a cell or tissue culture is used as the recipient tissue for transformation, plants can be regenerated from transformed cultures if desired, by techniques known to those skilled in the art. See, e.g., Niu et al., *Plant Cell Rep.* V19:304-310 (2000); Chang and Yang, *Bot. Bull. Acad. Sin.*, V37:35-40 (1996) and Han et al., *Biotechnology in Agriculture and Forestry*, V44:291 (ed. by Y. P. S. Bajaj), Springer-Vernag, (1999).

Genetically Modified (Transgenic) Plants/Plant Species/Plant Cells/Plant Tissues Also disclosed herein are genetically modified plants and plant cells that express an exogenous nucleic acid encoding a LecRLK1 variant or homolog, where the genetically modified plants and plant cells display increased mychorrization compared to plants which have not been modified.

In some embodiments, the genetically modified plant expresses an exogenous nucleic acid encoding a LecRLK1 variant or homolog. In some embodiments, the LecRLK1 variant or homolog is a *P. trichocarpa* LecRLK1 (PtLecRLK1) variant or homolog. In some embodiments, the PtLecRLK1 variant or homolog comprises an amino acid sequence shown by SEQ ID NO: 78. In some embodiments, the exogenous nucleic acid is stably transfected or transformed into the plant genome. In some embodiments, the exogenous nucleic acid is expressed constitutively in the genetically modified plant.

In some embodiments a plant or plant cell is transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Typically, transgenic plant cells used in methods described herein constitute part or all of a whole plant. Such plants can be grown in a manner suitable for the species under consideration, either in a growth chamber, a greenhouse or in a field. Transgenic plants can be bred as desired for a particular purpose, e.g., to introduce a recombinant nucleic acid into other lines, to transfer a recombinant nucleic acid to other species or for further selection of other desirable traits. Progeny includes descendants of a particular plant or plant line provided the progeny inherits the transgene. Progeny of a plant include seeds formed on F1, F2, F3, F4, F5, F6 and subsequent generation plants or seeds formed on BC1, BC2, BC3 and subsequent generation plants or seeds formed on F1BC1, F1BC2, F1BC3 and subsequent generation plants. Seeds produced by a transgenic plant can be grown and then selfed (or outcrossed and selfed) to obtain seeds homozygous for the nucleic acid construct. Alternatively, transgenic plants can be propagated vegetatively for those species amenable to such techniques.

Transgenic plant cells growing in suspension culture or tissue or organ culture can be useful for extraction of polypeptides or compounds of interest, e.g., lignin monomers or compounds in a lignin biosynthetic pathway. For the purposes of this invention, solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be any of various mineral salt media, e.g., Murashige and Skoog (MS) medium containing agar and a suitable concentration of an auxin, e.g., 2,4-dichlorophenoxyacetic acid (2,4-D) and a suitable concentration of a cytokinin, e.g., kinetin.

In some embodiments, the transgenic plants express the disclosed genes in a tissue-specific manner. In some embodiments, the genes are expressed from nucleic acid constructs that comprise a cell type or tissue type-preferential promoter. As used herein, a "cell type- or tissue-preferential promoter" refers to a promoter that drives expression preferentially in the target tissue, but may also lead to some expression in other cell types or tissues as well. In a specific embodiment, the disclosed genes are expressed in the leaf tissue.

Initial and immediate application of the disclosed methods can be made in the bioenergy crops *Populus* and switchgrass, but the application can be extended to other bioenergy crops such as corn, other sources of lignocellulosic biomass and other model plants e.g., Salix, *Miscanthus*, rice, wheat, soybean and *Medicago*.

For example, the polynucleotides and vectors described herein can be used to transform a number of monocotyledonous and dicotyledonous plants and plant cell systems, including alfalfa, ash, beech, birch, canola, cherry, clover, cotton, cottonseed, *eucalyptus*, flax, jatropha, mahogany, maple, mustard, oak, poplar, oilseed rape, rapeseed (high erucic acid and canola), red clover, teak, tomato, walnut and willow, as well as monocots such as barley, bluegrass, canarygrass, corn, fescue, field corn, millet, *miscanthus*, oat, rice, rye, ryegrass, sorghum, sudangrass, sugarcane, sweet corn, switchgrass, turf grasses, timothy and wheat. Gymnosperms such as fir, pine and spruce can also be suitable.

In some embodiments, the exogenous nucleic acid is expressed in the root tissue of the genetically-modified plant.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The specific examples listed below are only illustrative and by no means limiting.

EXAMPLES

Example 1: Materials and Methods

Identification of INDELs and Design of Primers.

One *P. trichocarpa* (93-968) and two *P. deltoides* (ILL-101 and D124) resequenced genomes were evaluated to identify and validate INDEL polymorphisms on chromosomes I and XI and to design PCR primers (Table 1).

TABLE 1

Primers used for targeted genotyping.

| Primers | |
|---|---|
| Genotyping primers | |
| Promoter-1990F | TTTCTCACTTTATGCTGGAA (SEQ ID NO: 1) |
| Promoter-1R | TGCTACTTTGATGATGTTTTCTTCT (SEQ ID NO: 2) |
| Promoter-1822F | ATTTCAAAGCCACCACCTAT (SEQ ID NO: 3) |
| Promoter-691R | TAACTTCCCACCCTAGCAATACAAGA (SEQ ID NO: 4) |
| Promoter-1609F | GTGCTCCAGTACAAGAAAGA (SEQ ID NO: 5) |
| Promoter-1202R | CTAAGTGATAGAGCGCATACTAATA (SEQ ID NO: 6) |

TABLE 1-continued

Primers used for targeted genotyping.

| Primers | |
|---|---|
| Gene + 440F | TCGAACATCCAACTGATACAA (SEQ ID NO: 7) |
| Gene + 2883R | TCAGATTCCTAAATGCATACGAAA (SEQ ID NO: 8) |
| Gene + 2583F | CACCAAACCAACTCTGAGTGAA (SEQ ID NO: 9) |
| Gene + 3784R | TTACCCAACATCAAAACTACATTCG (SEQ ID NO: 10) |
| Gene + 2556F | GCACACTTGGGTTGTCAGTGTTCAAGC (SEQ ID NO: 11) |
| Gene + 2901R | AATTCATTCCAGCTCTTATCAGATTCC (SEQ ID NO: 12) |
| PtUBCc | CTTGGACTGGCACTGTAATCGG (SEQ ID NO: 13), ACTGCTTTTGGTGATGGACTAAC (SEQ ID NO: 14) |
| Cloning primers | |
| CDS_T022200.1_for | CACCAAAATGCATTTCATTTCCATACTT (SEQ ID NO: 15) |
| CDS_T022200.1_wSTOP_rev | TTACCCAACATCAAAACTACATTCG (SEQ ID NO: 16) |
| CDS_T022200.1_w/oSTOP_rev | CCCAACATCAAAACTACATTCG (SEQ ID NO: 17) |
| RT-PCR primers | |
| PtLecRLK1 | GAAGGAAGACCTGGAACTACCAT (SEQ ID NO: 18) and |
| | TCTCGAATTCCTAGAAAGCCTCT (SEQ ID NO: 19) |
| PtUBQ10b | GCCTTCGTGGTGGTTATTAAGC (SEQ ID NO: 20) and |
| | TCCAACAATGGCCAGTAAACAC (SEQ ID NO: 21) |
| AtACT8 | ATGAAGATTAAGGTCGTGGCA (SEQ ID NO: 22) and |
| | TCCGAGTTTGAAGAGGCTAC (SEQ ID NO: 23) |

TABLE 2

Forward Primers used for INDEL genotyping

| Position | Forward Primer |
|---|---|
| 15706025 | ATACACGGAGGATGGACAGG (SEQ ID NO: 24) |
| 15708372 | ACATGCCCAAGAAGGTTGAG (SEQ ID NO: 25) |
| 15708724 | GCTCAGTTCATAGTCCAACAAAA (SEQ ID NO: 26) |
| 15708909 | TCAGATTCCTAAATGCATACGAAA (SEQ ID NO: 27) |
| 15709574 | ATCATTGTTGCCATGGGTTT (SEQ ID NO: 28) |

TABLE 2-continued

Forward Primers used for INDEL genotyping

| Position | Forward Primer |
|---|---|
| 15709769 | CACATGCCAAGGTACCAAAA (SEQ ID NO: 29) |
| 15710768 | TGAAAGCCATCTCCAGAACA (SEQ ID NO: 30) |
| 16009582 | CCCAAATCGGTTACTTCCAA (SEQ ID NO: 31) |
| 16290023 | GATATTCAGGAGGGCGATCA (SEQ ID NO: 32) |
| 16380543 | CCTAGTTTTCTTGGGCATCG (SEQ ID NO: 33) |
| 16467713 | CAATGGACTTTGACTTGGATCA (SEQ ID NO: 34) |
| 16468136 | GCCACATTTTCTTCGTGGTT (SEQ ID NO: 35) |
| 16636982 | CGCTACTGGTTCCCGTGTAT (SEQ ID NO: 36) |
| 16653192 | TCCTGAAGCCACCAAAGATT (SEQ ID NO: 37) |
| 16653192 | GAGCTGTTGTGCCTGTGTGT (SEQ ID NO: 38) |
| 16659120 | ACGATTGAAGCGTGTGAATG (SEQ ID NO: 39) |
| 16659693 | TTGCCAAAGAGGGTTAGCAT (SEQ ID NO: 40) |
| 16666929 | TTTCATTAGGTGCAGCCATTA (SEQ ID NO: 41) |
| 17004849 | CTGCTGAACACTGCCATGAT (SEQ ID NO: 42) |
| 17283803 | GGAGAGCACTGCCTGGATAG (SEQ ID NO: 43) |
| 17284223 | TCTCCAGCAAAACCTGCCTA (SEQ ID NO: 44) |
| 17290970 | TGATCAAATGTAGCACTCTATCCAA (SEQ ID NO: 45) |
| 17292326 | TATTTGGACGCTGACATGGA (SEQ ID NO: 46) |
| 17292667 | ATGGCGTTCACTTTGATTGC (SEQ ID NO: 47) |
| 17293186 | CGTTGCGATTTACAGCCTAA (SEQ ID NO: 48) |
| 17509070 | ACCCTGTTAGGCATGCTGTC (SEQ ID NO: 49) |
| 17510780 | CAACAAAAGGGACTTTAATCTAAACA (SEQ ID NO: 50) |

TABLE 3

Reverse Primers used for INDEL genotyping

| Position | Reverse |
|---|---|
| 15706025 | GAATTGCCCCATCCTAGACA (SEQ ID NO: 51) |
| 15708372 | CGGACGTCTTCAGTTTTGGT (SEQ ID NO: 52) |
| 15708724 | GATTGCTCGTGGAATCCTTT (SEQ ID NO: 53) |
| 15708909 | CACCAAACCAACTCTGAGTGAA (SEQ ID NO: 54) |
| 15709574 | GCGTGCAGGACAATCAAATA (SEQ ID NO: 55) |
| 15709769 | TGGAAGCAGCAACAGAAAAA (SEQ ID NO: 56) |
| 15710768 | TAACGAAGGCTCGAAAGTG (SEQ ID NO: 57) |
| 16009582 | TGTCTTCGAGTTGAAACCAAA (SEQ ID NO: 58) |
| 16290023 | ATGAAACCCATGCCCATTC (SEQ ID NO: 59) |
| 16380543 | CACTGAAAAGCCCCAACATT (SEQ ID NO: 60) |

TABLE 3-continued

Reverse Primers used for INDEL genotyping

| Position | Reverse |
|---|---|
| 16467713 | AGAGGATGATTCTCCACCAAA (SEQ ID NO: 61) |
| 16468136 | TCGAGAGAGACTATTTGCAAGC (SEQ ID NO: 62) |
| 16636982 | TTGCACGAGCAGTAGCATTC (SEQ ID NO: 63) |
| 16653192 | TCCGTGATCAAAACAATGGA (SEQ ID NO: 64) |
| 16653192 | CCCATTAACCTGCCATTCAC (SEQ ID NO: 65) |
| 16659120 | CTACGTGGGAAAATGGATG (SEQ ID NO: 66) |
| 16659693 | TGCAGCTTCTCAAAGCAATG (SEQ ID NO: 67) |
| 16666929 | ACGACCGACTGGAGTTGAAT (SEQ ID NO: 68) |
| 17004849 | TGCCCAAGTTCTTGGTTTTC (SEQ ID NO: 69) |
| 17283803 | CCTATCGAGCATGGGATTGT (SEQ ID NO: 70) |
| 17284223 | CCTTTTGGGCCACAATGTT (SEQ ID NO: 71) |
| 17290970 | CAAAAGAGAGACAAGGAAGGACA (SEQ ID NO: 72) |
| 17292326 | TCGTTAAATGGCGAGTACGA (SEQ ID NO: 73) |
| 17292667 | TGGAACTTGCCTCTAGATTTGA (SEQ ID NO: 74) |
| 17293186 | CAACATCAAACAGCTCGTGA (SEQ ID NO: 75) |
| 17509070 | ACCTCGACCCAAGCATGTTA (SEQ ID NO: 76) |
| 17510780 | CCTATAAATTGTGAAATCCAGCTT (SEQ ID NO: 77) |

Primers amplifying the expected sequence present in *P. trichocarpa* and absent in *P. deltoides* genotypes were subsequently used to screen 60 *P. deltoides* genotypes collected from the Yadkin and Carney Fork river systems in North Carolina and Tennessee[3], as well as from the University of Florida Association Mapping population. In addition, 2 parental lines and 299 progeny from the MB pedigree were similarly screened. Twenty-seven primer pairs were selected and designed to target INDELs within 5', coding, intronic and 3' regions for PCR validation, with product sizes ranging from 100 to 1000 bp (See, Tables 2 and 3).

DNA Isolation and PCR Amplification.

PCR amplifications were performed in a reaction with 25 µL volume containing 10-50 ng of diploid DNA, 50 mM Tris-HCl, 1.5 mM $MgCl_2$, 0.5 mM dNTPs, 2 µM of each primer and 1.0 units of Taq polymerase, using a Gene-Amp PCR system 9700 DNA Thermal Cycler (Applied Biosystems, Foster City, Calif., USA). The thermal cycles consisted of the primary denaturing step at 94° C. for 5 min, followed by 35 cycles, each of which involved 35 s at 94° C., 30-50 s at the primer-specific annealing temperature and 35 s at 72° C., followed by a final extension phase of 7 min at 72° C. Amplification products were purified using a TIAN quick Midi Purification Kit (TIANGEN, USA) following the manufacturer's protocol. Sequencing reactions were designed to cover the whole PCR segment, using an ABI Prism BigDye Terminator Cycle v3.1 Sequencing Kit and an ABI3130x1 or 3730x1 Genetic Analyzer (Applied Biosystems).

Genotyping and Genetic Mapping

The *Populus* Illumina 5K array (Geraldes, A. et al., *Mol. Ecol. Resour.* 13, 306-323 (2013); Muchero, W. et al., Vol. 81 *Forestry Sciences* (ed Trevor Fenning) Ch. 25, 587-595 (2014)) was used to genotype two parental lines and 299 progenies from the 54B pedigree (Labbé, J. et al., *Tree Genet. Genomes* 7, 617-627 (2011)). For INDEL genotyping, primers described above (Tables 1-3) were used to amplify DNA from target genotypes. Samples were resolved at 80V for 30 min on 1.5-2.0% agarose gel. After validating 60 individuals of *P. deltoides*, the positive PCR products were sequenced. All sequences of the same locus were aligned with Mega 4.1 (Kumar, S. et al., *Brief. Bioinform.* 9, 299-306 (2008)). JoinMap 3.0 (Van Ooijen, J. et al., *Kyazma BV: Wageningen, Netherlands* (2009)) was used to construct the genetic linkage map using the species-specific INDELs and 1,744 segregating SNPs from the above assay. The Kosambi mapping function (Kosambi, D. D., *Ann. Eugenics* 12, 172-175 (1943)) was used to convert recombination frequencies to centiMorgans. A step-wise reduction of the LOD score from 7 to 3 with a maximum recombination of 45% was used to assign markers to linkage groups. Only markers showing the highest congruency were used in map construction. QTLs were detected as described previously (Muchero, W. et al., Vol. 81 *Forestry Sciences* (ed Trevor Fenning) Ch. 25, 587-595 (2014)).

*Populus* Genotyping for PtLecRLK1

Six primers spanning the promoter, coding, intronic regions of the PtLecRLK1 were designed as described above (Table 1). Genomic DNAs from 20 *P. trichocarpa* and 60 *P. deltoides* genotypes were extracted from 100 mg fresh leaf material using a DNeasy Plant Mini Kit (Qiagen). Samples were eluted with 100 µL buffer and subsequently diluted 10- to 20-fold in 10 mM TE-buffer, depending on PCR results using PtUBCc primers. Genotyping PCRs were performed using 2× DreamTaq Green PCR Master Mix (Thermo Fisher Scientific Inc.) in a total volume of 25 µL including 5 µL diluted PCR template and 0.4 µM of each primer. The following cycling conditions were applied: initial denaturation for 3 min at 95° C., followed by 35 cycles of 30 s 95° C., 30 s 58° C. and 1 min per 1000 bp at 72° C. and final elongation for 7 min at 72° C. To visualize PCR products on a 0.8% (w/v) ethidium bromide-stained agarose gel, aliquots of PCR reactions for promoter or gene fragments of each genotype were combined and run on the same gel. To verify the correctness and specificity of all six genotyping PCRs, fragments obtained with genotypes Nisqually-1 and BESC-292 were subcloned using the CloneJet PCR cloning Kit (Thermo Fisher Scientific Inc.) and sequenced.

Generation of *Arabidopsis* Transgenics

A 2,220 bp Nisqually-1 Potri.T022200 v3.0 (PtLecRLK1) coding sequence was synthesized and cloned into pUC57 by GenScript USA Inc. Twenty pg of the synthesized DNA was used as template to amplify Potri.T022200 CDS with and without the stop-codon with Phusion High Fidelity DNA Polymerase (Thermo Fisher Scientific Inc.). PCR products were subcloned into the pENTR™/D-TOPO® vector (Thermo Fisher Scientific Inc.) and resulting plasmid DNAs were verified by sequencing. Subsequently, PtLecRLK1-coding region in pENTR vector was transferred by LR reaction into the binary plant destination vectors pGWB402$\Omega^{ref\ 29}$ and pGWB405 ($P_{35S}$-attR1-attR2-sGFP-$T_{NOS}$) using the manufacturer's protocol (Thermo Fisher Scientific Inc.). *Agrobacterium tumefaciens* strain GV3101 (pMP90) was transformed with the binary plant expression plasmids and used to transform *Arabidopsis thaliana* ecotype Col-0 by floral dipping. Transformed T1 individuals were selected by plating surface sterilized and cold-treated (2 d at 4° C.) seeds on ½ MS-medium solidified with 0.8% (w/v) agar and supplemented with 1% (w/v) sucrose, 100 µg mL$^{-1}$ kanamycin and 100 µg mL$^{-1}$ cefotaxime. Two independent lines (#8, #10) with single T-DNA insertion (based on Kanamycin$^{+/-}$ 3:1 ratio) were selected for further studies. The expression of PtLecRLK1 transgene was validated by RT-PCR. Total RNA was extracted from leaves of 14-day-old transgenic *Arabidopsis* lines using the Invisorb® Spin Plant Mini Kit (STRATEC Molecular GmbH) according to the manufacturer's instructions. Five-hundred ng of total RNA were reverse transcribed using oligo(dT)$_{18}$ and RevertAid First Strand cDNA Synthesis Kit (Thermo Fisher Scientific Inc.). RT-PCR was performed using 2× DreamTaq Green PCR Master Mix (Thermo Fisher Scientific Inc.) in a total volume of 25 µL including cDNA template corresponding to 25 ng total RNA and 1 µM of each primer. The following cycling conditions were applied: initial denaturation for 2 min at 95° C., followed by 30 cycles of 20 s 95° C., 20 s 57° C. and 2.5 min at 72° C. with a final elongation step for 7 min at 72° C. Amplification of AtACTIN8 (At1g49240) served as a control.

RT-PCR Analysis of Induction of PtLecRLK1 by *L. bicolor*

Internode cutting of *P. trichocarpa* (genotype '101-74') of the 54B F1 pedigree parental lines were rooted and individually inoculated with a 1/9 (v/v) mixture of fungal inoculum and calcinated clay (Oil Dri US Special, Damolin, Denmark). *L. bicolor* S238N inoculum was produced by growing mycelium on a peat-vermiculite nutrient mixture in 1-L glass jars for 2 months in the dark at 25° C. and kept at 4° C. before use. Inoculated cuttings were grown for three months in the greenhouse at 15-28° C., 12-h photoperiod. Colonized roots were confirmed under a stereomicroscope and collected for RNA extraction. Approximately 100 mg of root tissues were used for RNA extraction by using Sigma spectrum plant RNA extraction kit with modified Cetyltrimethyl Ammonium Bromide (CTAB) extraction buffer (Sigma-Aldrich, St. Louis, Mo.). One µg of total RNA was used to generate cDNA by using the Rite aid reverse transcriptase following manufacturer's instruction (Thermo Fisher Scientific, Hudson, N.H.). DreamTaq enzyme solution mixture (Thermo Fisher Scientific) was used for PCR reaction together with 1 µl of 2× diluted cDNA and gene-specific primers (Tables 1-3). PCR reaction was performed as follows: denaturation at 95° C. for 2 min followed by 40 cycles (for amplifying PtLecRLK1) or 30 cycles (for amplifying PtUBQ10b, Potri.001G26300) of 95° C. for 30 second, 56° C. for 30 second and 72° C. for 20 second. Another step of 72° C. for 7 min was performed for final extension reaction. The PCR product was run on 1% agarose gel with TBE (45 mM Tris-borate, 1 mM EDTA) at 100V for 30 min Gel image was taken by ChemiDoc XRS+ software (BIO-RAD, Hercules, Calif.).

Plant Fungal Co-Culture

Free-living mycelia of *L. bicolor* isolate S238N, *Cenococcum geophilum* isolate PMiCG1 and *Hebeloma cavipes* isolate PMiHeb1 were grown for 10 d on cellophane-covered agar (12 g L$^{-1}$) plates containing sugar-reduced Pachlewski medium P20 (Müller, A. et al., *Front. Plant Sci.* 4, 332 (2013)). For *L. bicolor* co-cultivation, six-day-old *Arabidopsis* seedlings of wild-type Col-0 or transgenic lines expressing PtLecRLK1 were transferred from ½ MS plates to P20 plates with or without *L. bicolor* S238N inoculum. All seedlings were grown at 23±1° C. with 12 h photoperiod (~125 µmol photons m$^{-2}$s$^{-1}$). A minimum of 20 plants per genotype were used for the morphological and anatomical assays. In the lateral root formation assay, *L. bicolor*-containing agar blocks were placed ~1 cm away from the root tip on both sides of root. The number of lateral roots was counted ten days after co-cultivation.

Microscopic Observation

To evaluate the Hartig net formation and detect fungal structures, roots were sectioned and stained with UVitex 2B (Polysciences, Inc., Warrington, Pa.) or Alexafluor 488-WGA (Molecular Probes, Inc., Eugene, Oreg.) and propidium iodide (ThermoFisher Scientific, Waltham, Mass.). Approximately 1-cm long root tips from *Arabidopsis* seedlings, which were grown with or without *L. bicolor* S238N for two weeks, were fixed in 4% (w/v) para-formaldehyde in phosphate-buffered saline (PBS; pH 7) overnight at 4° C. Roots were washed in PBS and embedded in 3% (w/v) agarose. Twenty-micrometer transverse sections were prepared using a microtome RM2245 (Leica Biosystems, Wetzlar, Germany) Sections were stained in 1% (w/v) UVitex 2B or Alexafluor 488-WGA and 20 mM propidium iodide in PBS for 2 min and then washed. All samples were observed using Zeiss confocal microscopy imaging.

Metabolite Profiling

Seeds of *Arabidopsis* wild type Col-0 and PtLecRLK1 transgenic plants were germinated on ½ MS medium with 1% sucrose. Six-day-old seedlings were transferred to P20 medium with or without *L. bicolor* S238N inoculum and cultured for another six days. The whole seedlings were subsequently collected for metabolite profiling with three biological replicates. A separate set of samples were collected for RNAseq analysis as described below. For metabolite profiling, approximately 50-75 mg (fresh weight) of *Arabidopsis* seedlings were ground in liquid nitrogen with a mortar and pestle and then twice extracted with 2.5 ml 80% ethanol overnight with extracts then combined prior to drying a 1.0-ml aliquot in a nitrogen stream. Sorbitol was added before extraction as an internal standard. Dried extracts were dissolved in acetonitrile followed by trimethylsilylation (TMS) and analysis after 2 d by GC-MS with instrument operating conditions and data extraction as described previously (Tschaplinski, T. J. et al., *Biotechnol. Biofuels* 5, 71 (2012)), except 2.5 full spectrum (50-650 Da) scans/s were used. Metabolites were identified by database matching with the Wiley Registry 10th Edition combined with NIST 2014 mass spectral database and a large user-created database (>2300 spectra) of mass spectral electron impact fragmentation patterns of TMS-derivatized compounds. Unidentified metabolites were denoted by their retention time (RT; min) and key mass-to-charge (m/z) ratios. Metabolite concentrations were normalized to the quantity of the internal standard recovered, volume of sample extracted, derivatized, and injected. The analysis included three biological replicates. Treatment means were tested for statistical significance (p<0.05) using Student t-tests.

RNAseq Analysis

The experiment set up for collecting samples for RNAseq was same as that of metabolite profiling described above. Total RNA was extracted from seedlings using the Invisorb® Spin Plant Mini Kit (STRATEC Molecular GmbH) according to the manufacturer's instructions, and sent to the Joint Genome Institute (JGI) for library construction and sequencing. Sequencing was performed using Illumina. Raw FASTQ file reads were filtered and trimmed using the JGI QC pipeline resulting in the filtered FASTQ file. Using BBDuk, raw reads were evaluated for artifact sequence by kmer matching (kmer=25), allowing 1 mismatch and detected artifact was trimmed from the 3' end of the reads. RNA spike-in reads, PhiX reads and reads containing any Ns were removed. Quality trimming was performed using the phred trimming method set at Q6. Finally, following trimming, reads under the length threshold were removed (minimum length 25 bases or ⅓ of the original read length— whichever is longer). Filtered reads from each library were aligned to the reference genome using HISAT version 0.1.4-beta (BAMs/directory). The command "featureCounts" was used to generate the raw gene counts using gff3 annotations. Only primary hits assigned to the reverse strand were included in the raw gene counts. Raw gene counts were used to evaluate the level of correlation between biological replicates using Pearson's correlation. DESeq2 (version 1.8.1) was subsequently used to determine differentially expressed genes (DEG) between pairs of conditions (p-value <0.05).

Data Availability

Data that support the findings of this application have been deposited into public repositories. The transcriptomics data has been deposited by JGI at GenBank under the accession code SRP117109.

Example 2: Identification of PtLecRLK1 Locus as a *Populus-Laccaria* QTL

The inventors hypothesized the existence of distinct genetic loci that are present in *P. trichocarpa* but absent in *P. deltoides* and harbor high-fidelity recognition mechanisms for *L. bicolor*.

To test these hypotheses, quantitative trait loci (QTL) previously identified in an interspecific *Populus* 54B $F_1$ pedigree for *L. bicolor* colonization (Labbé, J. et al., *Tree Genet. Genomes* 7, 617-627 (2011)) were evaluated. Multiple phenotypic datasets from the QTL study exhibited bimodal distributions, suggestive of a major QTL segregating in the population, and included four genomic regions, ranging from 1.7 Mb to 15 Mb on linkage groups I, II, III and XI, reproducibly identified across three independent experiments. The QTL resolution was subsequently improved by genotyping the two parental lines and 299 progeny from the 54B pedigree using the *Populus* 5K Illumina single nucleotide polymorphisms (SNP) array (Geraldes, A. et al., *Mol. Ecol. Resour.* 13, 306-323 (2013); Muchero, W. et al., Vol. 81 *Forestry Sciences* (ed Trevor Fenning) Ch. 25, 587-595 (2014)), which produced 1,744 segregating SNPs with less than 5% missing data. Of these, 677 SNPs were successfully incorporated into the genetic map, and on the basis of Multiple QTL Model mapping analyses, two of the four previously identified QTLs (Labbé, J. et al., *Tree Genet. Genomes* 7, 617-627 (2011)) were confirmed. The QTL on chromosome XI had the largest contribution, explaining up to 71% of the phenotypic variance across three different experiments. On the basis of marker segregation, it was determined that the beneficial allele was derived from the *L. bicolor*-favored *P. trichocarpa* parent. Because the physical positions of SNPs were available in the *Populus* reference genome v2.2, the inventors were able to resolve QTL on chromosome XI to a region harboring tandemly repeated receptor-like kinase genes.

This QTL interval was fine mapped with 27 PCR probes targeting insertion/deletion (INDEL) polymorphisms in this region and tested each locus against 20 *P. trichocarpa* and 60 *P. deltoides* genotypes. Of the 27 loci, two INDELs occurred within a single locus, POPTR_0011s13000 v2.2 (a.k.a., Potri.T022200 v3.0) and exhibited strong species-specificity, such that they were consistently absent in *P. deltoides* but present in all *P. trichocarpa* genotypes. The extent of the structural variation in this locus was further assessed by designing six additional primers spanning the coding and promoter regions and PCR confirmed that all 60 tested *P. deltoides* genotypes lacked this locus. Subsequently, sequence conservation of this locus was established across 917 *P. trichocarpa* genotypes (Slavov, G. T. et al., *New Phytol.* 196, 713-725 (2012); Evans, L. M. et al., *Nat. Genet.* 46, 1089-1096 (2014); Muchero, W. et al., *BMC Genomics* 16, 24 (2015)). Segregation analysis in the 54B pedigree also confirmed co-location of these INDELs with the QTL peak on LGXI and bulked-segregant analysis showed that progeny carrying this gene exhibited twice the colonization rate compared to ones lacking this gene (FIG. 1). This unambiguous conservation suggests that this locus is likely under species-specific purifying selection and that POPTR_0011s13000 encodes a positive regulator of *Populus-L. bicolor* colonization. These results are consistent with a previous report (Plett, J. M. et al., *New Phytol.* 202, 270-286 (2014)), where POPTR_0011 s13000 expression was reduced due to overexpression of the enzyme 1-aminocyclopropane-1-carboxylic acid oxidase and was correlated with a drastic reduction in Hartig net depth, a structure formed by ectomycorrhizal fungi. In addition, RT-PCR analysis confirmed the induction of POPTR_0011s13000 transcript by *L. bicolor* inoculation.

Figures 2A, 2B:
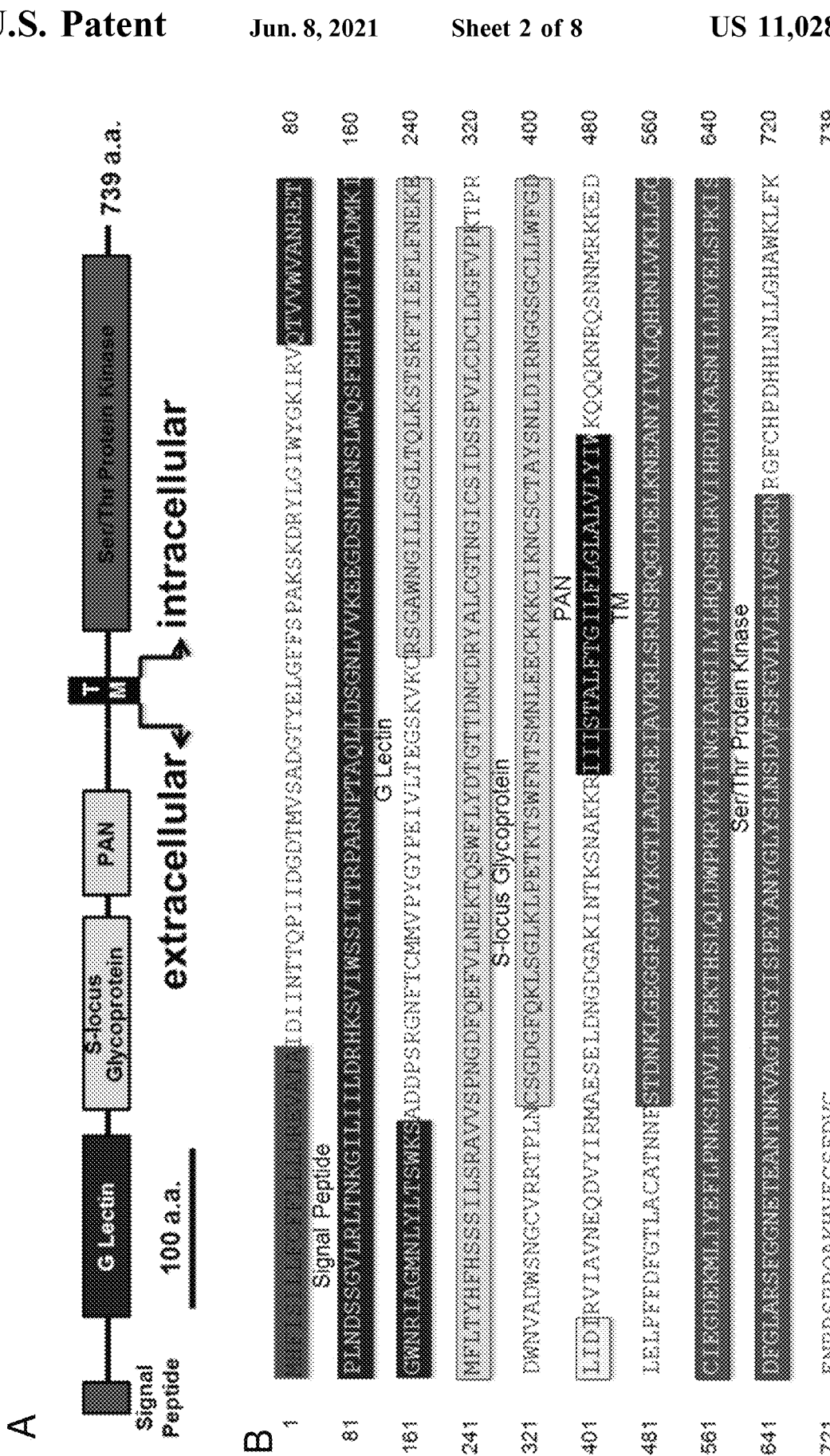
FIGS. 2A-2B. Sequence and domain structure of PtLecRLK1. (A) Schematic diagram of the PtLecRLK1 protein showing different domains. PAN, plasminogen/apple/nematode protein domain. TM, transmembrane domain. Motifs and domains were predicted by using Pfam v29.0, ScanProsite v20, and InterPro v56.0 based on HMMER. (B) Amino acid sequence of PtLecRLK1 (SEQ ID NO: 78) Amino acids are colored similarly to the corresponding protein domains shown in (A). Signal peptide was predicted by using SignalP v4.0. The location and orientation TM were predicted by using TMHMM (v2.0).

Functional annotation of POPTR_0011s13000 revealed a G-type lectin receptor-like kinase, hereafter designated as PtLecRLK1, a member of receptor-like kinase proteins implicated in the regulation of plant development, stress responses and innate immunity (Vaid, N. et al., *Mol. Plant* 6, 1405-1418 (2013); Singh, P. et al., *Front. Plant Sci.* 4, 124 (2013)). In a canonical manner, PtLecRLK1 contains an extracellular domain consisting of a G-lectin domain, an S-locus glycoprotein domain, a plasminogen/apple/nematode protein domain, a transmembrane domain and an intracellular serine/threonine protein kinase domain (FIG. 2A). In addition, at the N-terminus, the protein carries a hydrophobic segment of 22 amino acids, potentially acting as a signal peptide (FIG. 2B).

Example 3: Transgenic *Arabidopsis* Plants

Figures 3A, 3B:
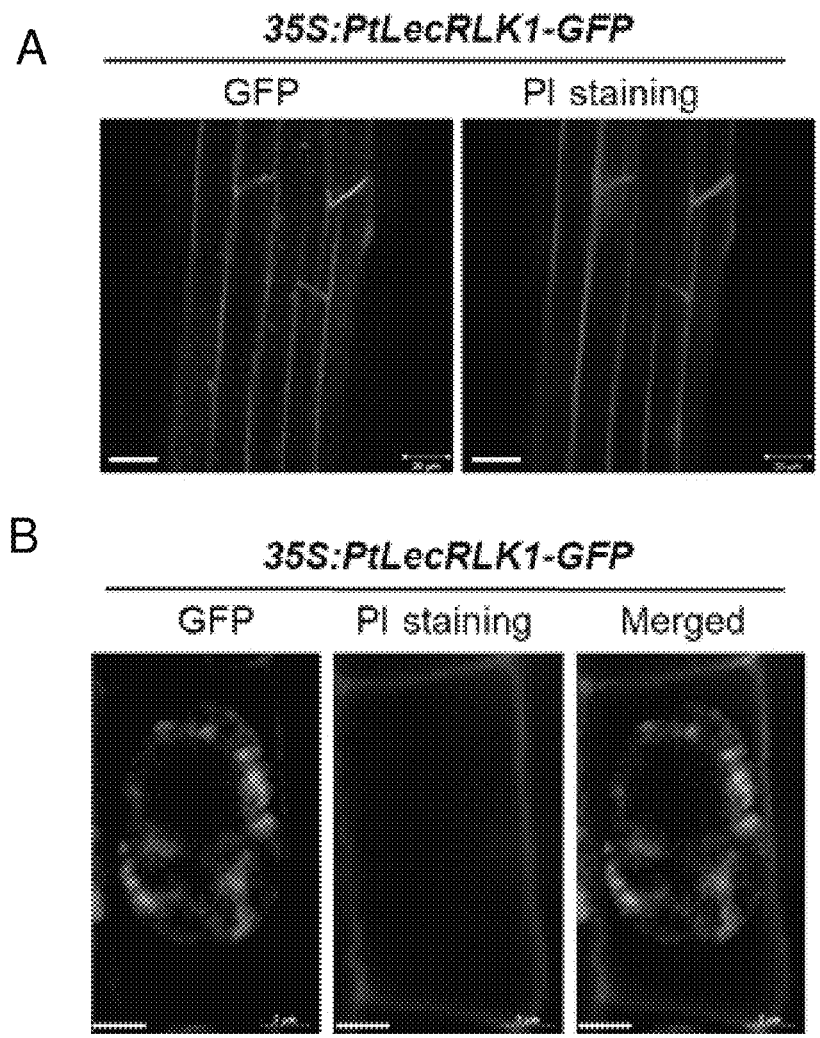
FIGS. 3A-3B. Subcellular location of PtLecRLK1 in *Arabidopsis* transgenic lines. (A) Subcellular localization analysis using the *Arabidopsis* transgenic lines expressing 35S:PtLecRLK1-GFP (left). Propidium iodide (PI) was used to stain root cell walls (right). (B) Plasmolysis analysis of *Arabidopsis* transgenic lines expressing 35S:PtLecRLK1-GFP. Mannitol (0.8 M; 30 min) was used to induce plasmolysis.

By using *Arabidopsis* transgenic plants expressing 35S:PtLecRLK1-GFP, it was found that GFP fluorescence signal was detected at the cell periphery (FIG. 3A). Upon plasmolysis of root epidermal cells of 35S:PtLecRLK1-GFP transgenic plants, GFP fluorescence signal was mostly detected in the cytosol (FIG. 3B), implying a potential induced-endocytic process of PtLecRLK1 protein under osmotic conditions given that PtLecRLK1 protein was predicted to contain transmembrane motif (FIG. 2A).

The establishment of an ectomycorrhizal symbiosis requires numerous coordinated processes leading to the development of new fungal or host structures. Such changes require an orchestrated co-response between the host and its symbiont through the exchange of various signaling molecules. Several hundreds of symbiosis-regulated genes have been identified in ectomycorrhizal fungi in association with their hosts (Plett, J. M. et al., *Curr. Biol.* 21, 1197-1203 (2011)). Through transcriptomics analysis of differentially expressed genes in Col-0 wild type and 35S:PtLecRLK1 transgenic lines with and without *L. bicolor* inoculation, the inventors found that *L. bicolor* inoculation resulted in upregulation of nine defense-related genes in Col-0 but only two in the PtLecRLK1 transgenic lines (FIG. 4A-FIG. 4F). More importantly, *L. bicolor* inoculation resulted in downregulation of 24 defense-related genes in 35S:PtLecRLK1 transgenic plants (vs one in Col-0) (FIGS. 4E and 4F). The relative low number of defense-related genes detected in this study is likely due to the inoculation method (i.e., no direct contact between the *L. bicolor* hyphae and the root in the beginning of inoculation) and the relatively short inoculation time (i.e., 6 days).

Inoculation of wild-type Col-0 with *L. bicolor* also triggered alterations in a number of metabolites (Table 4). However, many of these metabolic changes were diminished in the transgenic plants expressing PtLecRLK1 (Table 1).

TABLE 4

Metabolite profiles of wild-type Col-0 and 35S:PtLecRLK1 transgenic plants co-cultivated with *L. bicolor*. Only metabolites that are significantly altered (p ≤ 0.05) by *L. bicolor* inoculation in the wild type Col-0 or the 35S:PtLecRLK1 transgenic plants (line #8) are shown. Shown are mean values of three biological replicates.

| Metabolite | Col ± *Laccaria* Fold change | p-value | 35S:PtLecRLK1 ± *Laccaria* Fold change | P-value |
|---|---|---|---|---|
| histidine | 22.41 | 0.001 | 2.26 | 0.011 |
| sinapoyl malate | 8.30 | 0.000 | 1.62 | 0.007 |
| myo-inositol | 8.03 | 0.000 | 2.10 | 0.086 |
| 12.26 362 | 7.02 | 0.012 | 3.71 | 0.001 |
| coniferin | 6.62 | 0.000 | 1.96 | 0.055 |
| syringin | 4.76 | 0.001 | 2.32 | 0.007 |
| sucrose | 4.45 | 0.000 | 1.58 | 0.009 |
| 17.15 297 279 | 3.78 | 0.000 | 1.80 | 0.015 |
| hexacosanoic acid | 3.57 | 0.030 | 1.16 | 0.580 |
| glucose | 2.39 | 0.001 | 1.38 | 0.055 |
| kaempferol | 2.23 | 0.002 | 1.47 | 0.096 |
| cholesterol | 2.22 | 0.023 | 1.01 | 0.953 |
| 15.05 197 glyc | 2.14 | 0.011 | 1.21 | 0.314 |
| phytol | 2.01 | 0.008 | 1.39 | 0.088 |
| 14.14 299 503 | 1.80 | 0.002 | 1.35 | 0.055 |
| 11.53 435 345 | 1.76 | 0.004 | 1.40 | 0.084 |
| quercetin | 1.65 | 0.008 | 1.17 | 0.425 |
| 11.63 435 345 | 1.62 | 0.004 | 1.44 | 0.060 |
| glucose 6-phosphate | 1.48 | 0.045 | 1.22 | 0.154 |
| 13.13 409 | 1.39 | 0.031 | 1.30 | 0.110 |
| campesterol | 1.30 | 0.046 | 1.06 | 0.598 |
| 10.74 227 GLN-like | 1.22 | 0.194 | 1.90 | 0.007 |
| asparagine | 1.03 | 0.816 | 1.33 | 0.002 |
| putrescine | 1.02 | 0.911 | 1.65 | 0.006 |
| GABA | 0.98 | 0.905 | 1.58 | 0.019 |
| 5-oxo-proline | 0.94 | 0.678 | 1.29 | 0.023 |
| sinapic acid | 0.88 | 0.470 | 0.79 | 0.049 |
| brassidic acid | 0.83 | 0.611 | 0.42 | 0.036 |
| aspartic acid | 0.70 | 0.029 | 0.95 | 0.530 |
| malic acid | 0.62 | 0.029 | 0.68 | 0.032 |
| salicylic acid | 0.62 | 0.034 | 0.97 | 0.851 |
| tryptophan | 0.61 | 0.033 | 0.90 | 0.539 |
| 12 232 347 449 | 0.60 | 0.010 | 0.98 | 0.901 |
| uric acid | 0.57 | 0.010 | 0.60 | 0.035 |
| cysteine | 0.56 | 0.019 | 0.96 | 0.856 |
| alanine | 0.56 | 0.016 | 0.71 | 0.127 |
| palmitic-acid | 0.55 | 0.000 | 0.80 | 0.237 |
| 9.31 155 | 0.51 | 0.014 | 1.01 | 0.974 |
| 12.31 362 | 0.49 | 0.003 | 0.74 | 0.238 |
| 12.71 320 | 0.38 | 0.001 | 0.72 | 0.199 |
| stearic acid | 0.38 | 0.000 | 0.68 | 0.097 |
| 12.24 230 227 | 0.38 | 0.000 | 0.53 | 0.062 |
| 12.76 320 | 0.38 | 0.002 | 0.71 | 0.206 |
| 15.2 411 426 glyc | 0.35 | 0.015 | 0.78 | 0.220 |
| B-cyano-alanine | 0.35 | 0.011 | 0.64 | 0.017 |
| glycine | 0.32 | 0.020 | 0.29 | 0.001 |
| 12.42 320 | 0.29 | 0.001 | 0.59 | 0.130 |
| 14.06 320 | 0.28 | 0.003 | 0.56 | 0.044 |
| 12.20 320 | 0.27 | 0.008 | 0.65 | 0.095 |
| 4-hydroxybenzoic acid | 0.27 | 0.013 | 0.67 | 0.050 |
| 12.83 362 | 0.25 | 0.009 | 0.50 | 0.085 |
| dihydrouracil | 0.25 | 0.003 | 0.60 | 0.117 |
| 12.48 320 | 0.23 | 0.020 | 0.67 | 0.214 |
| 12.52 320 | 0.23 | 0.009 | 0.68 | 0.190 |
| 9.78 98 | 0.21 | 0.005 | 0.51 | 0.061 |
| azelaic acid | 0.15 | 0.002 | 0.46 | 0.010 |
| 3-hydroxybenzoic | 0.13 | 0.010 | 0.36 | 0.010 |

TABLE 4-continued

Metabolite profiles of wild-type Col-0 and 35S:PtLecRLK1 transgenic plants co-cultivated with L. bicolor. Only metabolites that are significantly altered (p ≤ 0.05) by L. bicolor inoculation in the wild type Col-0 or the 35S:PtLecRLK1 transgenic plants (line #8) are shown. Shown are mean values of three biological replicates.

| Metabolite | Col ± Laccaria | | 35S:PtLecRLK1 ± Laccaria | |
|---|---|---|---|---|
| | Fold change | p-value | Fold change | P-value |
| acid | | | | |
| isoleucine | 0.12 | 0.003 | 0.27 | 0.264 |
| 12.31 507 | 0.09 | 0.002 | 0.42 | 0.065 |
| 7.87 249 | 0.03 | 0.000 | 0.24 | 0.100 |
| 12.39 320 | 0.00 | 0.000 | 0.00 | 0.206 |

The large-scale *L. bicolor*-induced, up-regulated metabolite defense responses in wild-type *Arabidopsis* (i.e., histidine, sinapoyl malate, sinapoyl-4-O-glucoside, syringin, coniferin, hexacosanoic acid, kaempferol, cholesterol and other sinapoyl conjugates) were significantly reduced in the transgenic plants, a trend that is similar to that observed between *L. bicolor*-incompatible host *P. deltoides* and -compatible host *P. trichocarpa* though the exact defense-related metabolites differed between *Arabidopsis* and *Populus* (Tschaplinski, T. J. et al., *Mol. Plant Microbe Interact.* 27, 546-556 (2014)). Furthermore, the down-regulation of amino acids, fatty acids and organic acids in wild-type plants in response to *L. bicolor*, which are often attributed to symbiont utilization and are likely due to altered host carbon partitioning to up-regulated defense responses 16, were also muted in the transgenic plants (Table 4).

In both the *Populus-L. bicolor* and now the transgenic *Arabidopsis-L. bicolor* systems, the inventors found that plant-fungus interaction is mediated by a G-type lectin receptor-like kinase. Receptor-like kinases have been shown to govern perception of pathogens (Wu, Y. et al., *J. Integr. Plant BioL* 55, 1271-1286 (2013); Antolín-Llovera, M. et al., *New Phytol.* 204, 791-802 (2014); Ranf, S. et al., *Nat. Immunol.* 16, 426-433 (2015)). Here, the inventors have identified PtLecRLK1 as a key regulator of fungal root colonization. This disclosure reveals a role of plant lectin receptor-like kinase in the mycorrhizal symbiosis and demonstrates the importance of this protein in plant-microbe interactions. One implication of this work is that the design of host-microbe symbioses into non-host organisms is feasible. In particular, PtLecRLK1 provides an immediate target for rational design of mycorrhizal symbiosis in economically important crops to enhance water and nutrient acquisition in marginal lands.

What is claimed is:

1. A method for improving mycorrhization in a plant or plant cell, comprising expressing an exogenous nucleic acid encoding a Lectin receptor-like kinase 1 (LecRLKI) variant or homolog in the plant or plant cell, wherein the expression of the LecRKL1 variant or homolog improves mycorrhizal symbiosis in the plant or plant cell, and wherein the LecRLKI variant or homolog comprises an amino acid sequence that is at least 98% identical to the amino acid sequence shown by SEQ ID NO: 78.

2. The method of claim 1, wherein the exogenous nucleic acid encoding the LecRLK1 variant or homolog is stably transfected or transformed into the plant genome.

3. The method of claim 1, wherein the exogenous nucleic acid encoding LecRLK1 the LecRLK1 variant or homolog is expressed in the root tissue of the plant.

4. The method of claim 3, wherein the root-specific expression is achieved by a root-specific promoter selected from the group consisting of a Death Receptor 5 (DR5) promoter, a *Populus trichocarpa* developing phloem 3 (PtrDP3) promoter and a *Populus trichocarpa* mature xylem 3 (PtrMX3) promoter.

5. The method according to claim 1, wherein the plant is selected from the group consisting of genera *Allium, Arabidopsis, Brassica, Capsicum, Citrullus, Cucumis, Eucalyptus, Fragaria, Glycine, Gossypium, Hordeum, Ipomoea, Malus, Manihot, Nicotiana, Oryza, Populus, Prunus, Rosa, Solanum, Spinacia, Triticum, Panicum, Saccharum, Setaria, Sorghum, Zea, Kalanchoe Phalaenopsis, Ananas* and *Crassula*.

6. A genetically modified plant or plant cell comprising an exogenous nucleic acid encoding a Lectin receptor-like kinase 1 (LecRLK1) variant or homolog in the plant or plant cell, wherein the LecRLK1 variant or homolog is expressed in the plant or plant cell, and wherein the LecRLK1 variant or homolog comprises an amino acid sequence that is at least 98% identitical to the amino acid sequence shown by SEQ ID NO: 78.

7. The genetically-modified plant or plant cell of claim 6, wherein the exogenous nucleic acid is stably transfected or transformed into the plant genome.

8. The genetically-modified plant or plant cell of claim 6, wherein the exogenous nucleic acid is expressed in the root tissue of the plant.

9. An expression vector comprising a nucleotide sequence encoding a Lectin receptor-like kinase 1 (LecRLK1) allelic variant or homolog operably linked to a heterologous regulatory region that is functional in a plant or plant cell, wherein the LecRLK1 variant or homolog comprises an amino acid sequence that is at least 98% identical to the amino acid sequence shown by SEQ ID NO: 78.

10. The expression vector of claim 9, wherein the regulatory region comprises a promoter selected from the group consisting of a constitutive promoter, a tissue-specific promoter, and a regulated promoter.

11. The expression vector of claim 10, wherein the tissue-specific promoter is a root-specific promoter.

12. The expression vector of claim 11, wherein the root-specific promoter is selected from the group consisting of a Death Receptor 5 (DR5) promoter, a *Populus trichocarpa* developing phloem 3 (PtrDP3) promoter and a *Populus trichocarpa* mature xylem 3 (PtrMX3) promoter.

13. The expression vector of claim 10, wherein the constitutive promoter is selected from the group consisting of a ubiquitin promoter, a cauliflower mosaic virus (CaMV) 35S promoter, a nopaline synthase (nos) promoter, an actin promoter, a peanut chlorotic streak caulimovirus promoter, a *Chlorella* virus methyltransferase gene promoter, a full-length transcript promoter form figwort mosaic virus, a pEMU promoter, a MAS promoter, a maize H3 histone promoter and an *Agrobacterium* gene promoter.

14. The expression vector of claim 10, wherein the regulated promoter is selected from the group consisting of a stress induced promoter, a chemical-induced promoter, a light induced promoter, a dark-induced promoter, and a circadian-clock controlled promoter.

15. A method for improving mycorrhization in a plant or plant cell, comprising introducing the expression vector of claim 13 into a plant or plant cell, and expressing the nucleotide sequence in the plant or plant cell, wherein the expression of the LecRKL1 variant or homolog improves mycorrhizal symbiosis in the plant or plant cell.

16. A plant or plant cell comprising the expression vector of claim 9.

17. The method of claim 1, wherein the LecRLK1 variant or homolog comprises a signal peptide sequence that is identical to amino acids 1-22 of SEQ ID NO: 78, a G-lectin domain sequence that is identical to amino acids 69-177 of SEQ ID NO: 78, a PAN domain sequence that is identical to amino acids 209-316 of SEQ ID NO: 78, a transmembrane domain sequence that is identical to amino acids 441-463 of SEQ ID NO: 78, and a Ser/Thr protein kinase domain sequence that is identical to amino acids 499-699 of SEQ ID NO: 78.

18. The genetically-modified plant or plant cell of claim 6, wherein the LecRLK1 variant or homolog comprises a signal peptide sequence that is identical to amino acids 1-22 of SEQ ID NO: 78, a G-lectin domain sequence that is identical to amino acids 69-177 of SEQ ID NO: 78, a PAN domain sequence that is identical to amino acids 209-316 of SEQ ID NO: 78, a transmembrane domain sequence that is identical to amino acids 441-463 of SEQ ID NO: 78, and a Ser/Thr protein kinase domain sequence that is identical to amino acids 499-699 of SEQ ID NO: 78.

19. The expression vector of claim 9, wherein the LecRLK1 variant or homolog comprises a signal peptide sequence that is identical to amino acids 1-22 of SEQ ID NO: 78, a G-lectin domain sequence that is identical to amino acids 69-177 of SEQ ID NO: 78, a PAN domain sequence that is identical to amino acids 209-316 of SEQ ID NO: 78, a transmembrane domain sequence that is identical to amino acids 441-463 of SEQ ID NO: 78, and a Ser/Thr protein kinase domain sequence that is identical to amino acids 499-699 of SEQ ID NO: 78.

* * * * *